US006232462B1

(12) United States Patent
Collins et al.

(10) Patent No.: US 6,232,462 B1
(45) Date of Patent: May 15, 2001

(54) REDUCTION OF NONSPECIFIC HYBRIDIZATION BY USING NOVEL BASE-PAIRING SCHEMES

(75) Inventors: Mark L. Collins, Walnut Creek; Thomas Horn, Berkeley; Patrick J Sheridan, San Leandro; Brian D. Warner, Martinez; Michael S. Urdea, Alamo, all of CA (US)

(73) Assignee: Bayer Corporation, East Walpole, MA (US)

( * ) Notice: Subject to any disclaimer, the term of this patent is extended or adjusted under 35 U.S.C. 154(b) by 0 days.

(21) Appl. No.: 09/115,566

(22) Filed: Jul. 14, 1998

Related U.S. Application Data

(63) Continuation of application No. 08/794,153, filed on Feb. 3, 1997, now Pat. No. 5,780,610, which is a continuation of application No. 08/435,547, filed on May 5, 1995, now abandoned, which is a continuation of application No. 08/298,073, filed on Aug. 30, 1994, now Pat. No. 5,681,002.

(51) Int. Cl.[7] .......................... C07H 21/00; C07H 21/04; C07H 21/02
(52) U.S. Cl. ...................... 536/25.3; 536/24.3; 536/24.5
(58) Field of Search .................. 536/25.3, 23.1, 536/24.5

(56) References Cited

U.S. PATENT DOCUMENTS

| 4,868,105 | 9/1989 | Urdea et al. . |
| 5,124,246 | 6/1992 | Urdea et al. . |
| 5,135,917 | 8/1992 | Burch . |
| 5,270,163 | 12/1993 | Gold et al. . |

FOREIGN PATENT DOCUMENTS 0070 685 A2  1/1983  (EP) .

OTHER PUBLICATIONS

Divakar et al, "Conversion of guanosine into isoguanosine and derivatives", J. Chem. Soc. Perkin Trans. 1: 771–774, 1991.*
Ogilivie et al, "The synthesis of oligoribonucleotides. III. The use of silyl protecting groups in nucleoside and nucleotide chemistry", Can. J. Chem. 57:2230–2238, 1979.*
Bain et al., "Ribosome Mediated Incorporation of a Non–Standard Amino Acid Into a Peptide Through Expansion of the Genetic Code," Nature 356:537–539 (1992).
Chern et al., "A Novel and Efficient Synthesis of Isoguanosine," Tetrahedron Lett. 28(19):2151–2154 (1987).

Horn et al., "Hybridization Properties of the 5–Methyl–Isocytidine/Isoguanosine Base Pair in Synthetic Oligonucleotides," Tetrahedron Lett. 36(12):2033–2036 (1995).
Kazimierczuk et al., "2–Deoxyisoguanosine and Base–Modified Analogues: Chemical and Photochemical Synthesis," Helv. Chim. Acta 74:1742–1748 (1991).
Latham et al., "The Application of a Modified Nucleotide in Aptamer Selection: Novel Thrombin Aptamers Containing 5–(1–Pentynyl–2'–Deoxyuridine," Nucleic Acids Res. 22(14):2817–2822 (1994).
Leach et al., "Theoretical Investigations of Novel Nucleic Acid Bases," J. Am. Chem. Soc. 114:3675–3683 (1992).
Mantsch et al., "Structural and Enzymatic Properties of Adenine I–Oxide Nucleotides," Biochem. 14:5593–5601 (1993).
Piccirilli et al., "Enzymatic Incorporation of a New Base Pair into DNA and RNA Extends the Genetic Alphabet," Nature 343:33–37 (1990).
Seela et al., "Synthesis of Phosphonates and Oligodeoxyribonucleotides Derived From 2'–Deoxyisoguanosine and 2'–Deoxy–2–Haloadenosines," Helv. Chim. Acta 75:2298–2306 (1992).
Stratagene Catalog, p. 39 (1988).
Switzer et al., "Enzymatic Incorporation of a New Base Pair Into DNA and RNA," J. Am. Chem. Soc. 111:8322–8323 (1989).
Switzer et al., "Enzymatic Recognition of the Base Pair Between Isocytidine and Isoguanosine," Biochemistry 32:10489–10496 (1993).
Tor et al., "Site–Specific Enzymatic Incorporation of an Unnatural Base, $N^6$–(6–Aminohexyl)isoguanosine, into RNA," J. Am. Chem. Soc. 115:4461–4467 (1993).
Voegel et al., "Nonstandard Hydrogen Bonding in Duplex Oligonucleotides. The Base Pair Between an Acceptor–Donor–Donor Pyrimidine Analog and Donor–Acceptor–Acceptor Purine Analog," J. Am. Chem. Soc. 116:6329–6930 (1994).

* cited by examiner

Primary Examiner—Jeffrey Fredman
(74) Attorney, Agent, or Firm—Dianne E. Reed; J. Elin Hartrum; Reed & Associates

(57) ABSTRACT

Methods are provided for substantially reducing background signals encountered in nucleic acid hybridization assays. The method is premised on the elimination or significant reduction of the phenomenon of nonspecific hybridization, so as to provide a detectable signal which is produced only in the presence the target polynucleotide of interest. In addition, a novel method for the chemical synthesis of isoguanosine or 2'-deoxy-isoguanosine is provided. The invention also has applications in antisense and aptamer therapeutics and drug discovery.

6 Claims, 2 Drawing Sheets

REDUCTION OF NONSPECIFIC HYBRIDIZATION BY USING NOVEL BASE-PAIRING SCHEMES

This application is a continuation of U.S. Ser. No. 08/794,153 filed Feb. 3, 1997, now U.S. Pat. No. 5,780,610 which is a continuation of U.S. Ser. No. 08/435,547, filed May 5, 1995, now abandoned, which is a continuation of U.S. Ser. No. 08/298,073, filed Aug. 30, 1994, now U.S. Pat. No. 5,681,002, issued Oct. 28, 1997.

TECHNICAL FIELD

This invention relates generally to nucleic acid chemistry and hybridization assays. More particularly, the invention relates to methods for generating a more target-dependent signal in nucleic acid hybridization assays by minimizing background noise deriving primarily from nonspecific hybridization. The invention also has applications in antisense and aptamer therapeutics and drug discovery.

BACKGROUND

Nucleic acid hybridization assays are commonly used in genetic research, biomedical research and clinical diagnostics. In a basic nucleic acid hybridization assay, single-stranded analyte nucleic acid is hybridized to a labeled single-stranded nucleic acid probe and resulting labeled duplexes are detected. Variations of this basic scheme have been developed to enhance accuracy, facilitate the separation of the duplexes to be detected from extraneous materials, and/or amplify the signal that is detected.

The present invention is directed to a method of reducing background noise encountered in any nucleic acid hybridization assay. Generally, the background noise which is addressed by way of the presently disclosed techniques results from undesirable interaction of various polynucleotide components that are used in a given assay, i.e., interaction which gives rise to a signal which does not correspond to the presence or quantity of analyte. The invention is useful in conjunction with any number of assay formats wherein multiple hybridization steps are carried out to produce a detectable signal which correlates with the presence or quantity of a polynucleotide analyte.

One such assay is described in detail in commonly assigned U.S. Pat. No. 4,868,105 to Urdea et al., the disclosure of which is incorporated herein by reference. That assay involves the use of a two-part capturing system designed to bind the polynucleotide analyte to a solid support, and a two-part labeling system designed to bind a detectable label to the polynucleotide analyte to be detected or quantitated. The two-part capture system involves the use of capture probes bound to a solid support and capture extender molecules which hybridize both to a segment of the capture probes and to a segment of the polynucleotide analyte. The two-part labelling system involves the use of label extender molecules which hybridize to a segment of the polynucleotide analyte, and labeled probes which hybridize to the label extender molecules and contain or bind to a detectable label. An advantage of such a system is that a plurality of hybridization steps must occur in order for label to be detected in a manner that correlates with the presence of the analyte, insofar as two distinct hybridization reactions must occur for analyte "capture," and, similarly, two distinct hybridization reactions must occur for analyte labelling. However, there remain a number of ways in which a detectable signal can be generated in a manner which does not correspond to the presence or quantity of analyte, and these will be discussed in detail below.

Another example of an assay with which the present invention is useful is a signal amplification method which is described in commonly assigned U.S. Pat. No. 5,124,246 to Urdea et al., the disclosure of which is incorporated herein by reference. In that method, the signal is amplified through the use of amplification multimers, polynucleotides which are constructed so as to contain a first segment that hybridizes specifically to the label extenders, and a multiplicity of identical second segments that hybridize specifically to a labeled probe. The degree of amplification is theoretically proportional to the number of iterations of the second segment. The multimers may be either linear or branched. Branched multimers may be in the shape of a fork or a comb, with comb-type multimers preferred.

One approach to solving the problem of interfering background signals in nucleic acid hybridization assays is provided in commonly assigned U.S. patent application Ser. No. 08/164,388 to Urdea et al. in which at least two capture extenders and/or two or more label extenders must bind to the analyte in order to trigger a detectable signal. To further reduce background noise, the assay is conducted under conditions which favor the formation of multicomponent complexes.

Another approach which has been proposed to increase the target dependence of the signal in a hybridization assay is described in European Patent Publication No. 70,685, inventors Heller et al. That reference describes a homogeneous hybridization assay in which a nonradiative transfer of energy occurs between proximal probes; two distinct events must occur for a target-generated signal to be produced, enhancing the accuracy of detection.

The present invention is also designed to increase the accuracy of detection and quantitation of polynucleotide analytes in hybridization assays. The invention increases both the sensitivity and specificity of such assays, by reducing the incidence of signal generation that occurs in the absence of target, and does not involve an increase in either time or cost relative to currently used assay configurations.

The goals of the present invention, namely to reduce background noise and to increase accuracy of detection and quantitation of analytes in nucleic acid hybridization assays have been achieved, in part, by the use of nucleoside variants that form base pairs by virtue of "non-natural" hydrogen bonding patterns. As used herein, a "non-natural" base pair is one formed between nucleotidic units other than adenosine (A), thymidine (T), cytidine (C), guanosine (G) or uridine (U). One such non-natural nucleoside base pair is formed between isocytosine (isoC) and isoguanine (isoG). IsoC and isoG can form a base pair with a standard geometry (i.e., a "Watson-Crick base pair") but involving hydrogen bonding other than that involved in the bonding of cytosine (C) to guanine (G), as shown below:

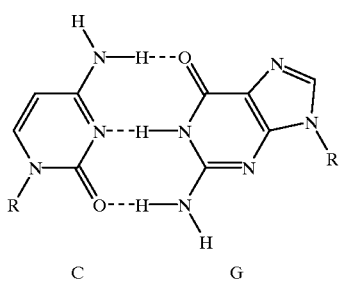

-continued

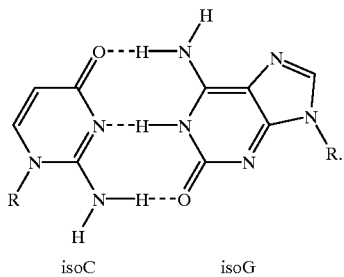

isoC        isoG

Leach et al. (1992) *J. Am. Chem. Soc.* 114:3675–3683 applied molecular mechanics, molecular dynamics and free energy perturbation calculations to study the structure and stability of the isoC*isoG base pair. Tor et al. (1993) *J. Am. Chem. Soc.* 115:4461–4467 describe a method whereby a modified isoc in a DNA template will direct the incorporation of an isoG analog into the transcribed RNA product. Switzer et al. (1993) *Biochemistry* 32:10489–10496 studied the conditions under which the base pair formed between isoC and isoG might be incorporated into DNA and RNA by DNA and RNA polymerases.

Introduction of a new base pair into DNA oligomers offers the potential of allowing more precise control over hybridization.

SUMMARY OF THE INVENTION

The present invention provides methods and kits for detecting nucleic acid analytes in a sample. In general, the methods represent improvements in nucleic acid hybridization assays, such as in situ hybridization assays, Southerns, Northerns, dot blots and polymerase chain reaction assays. In particular, the methods represent improvements on solution phase sandwich hybridization assays which involve binding the analyte to a solid support, labelling the analyte, and detecting the presence of label on the support. Preferred methods involve the use of amplification multimers which enable the binding of significantly more label in the analyte-probe complex, enhancing assay sensitivity and specificity.

In a first aspect of the invention, an assay is provided in which one or more nucleotidic units which are capable of forming base pairs and which are other than adenosine (A), thymidine (T), cytidine (C), guanosine (G) or uridine (U), are incorporated into non-target hybridizing oligonucleotide segments, i.e., "universal" segments, of nucleic acid hybridization assay components. This use of such nucleotidic units gives rise to unique base-pairing schemes which result in enhanced binding specificity between universal segments.

In a related aspect of the invention, an assay is provided in which at least one first nucleotidic unit other than A, T, C, G, or U capable of forming a base pair with a second nucleotidic unit other than A, T, C, G, or U, is incorporated into nucleic acid sequences of assay components which are complementary to nucleic acid sequences present in assay components other than the target molecule. Examples of base pairs formed between two such nucleotidic units are given in the following structures (I) to (IV):

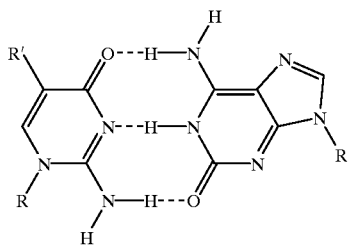

(I)

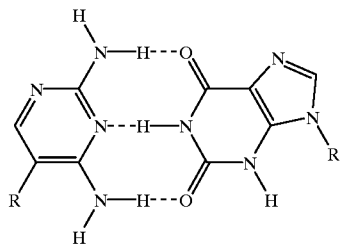

(II)

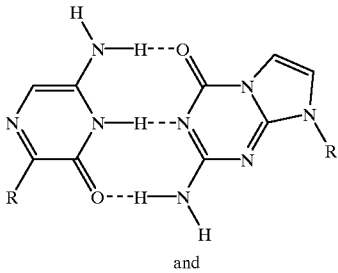

(III)

and

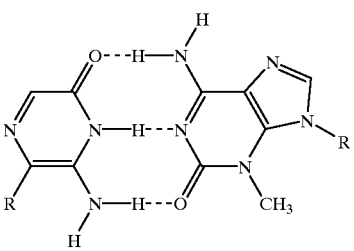

(IV)

wherein R represents a backbone which will allow the bases to form a base pair with a complementary nucleotidic unit when incorporated into a polynucleotide, and R' is, for example, hydrogen, methyl, α- or β-propynyl, bromine, fluorine, iodine, or the like. By incorporating such nucleotidic units into such so-called "universal" sequences, i.e., sequences not involved in hybridization to the target analyte, the potential for nonspecific hybridization is greatly reduced. In one preferred embodiment, the first and second nucleotidic units interchangeably consist of isocytidine and isoguanosine, as shown in Formula (I).

In a related aspect of the invention, an assay is provided in which the melt temperature $T_{m1}$ of the complex formed between the analyte and the support-bound capture probes, mediated by one or more distinct capture extender molecules, and/or the label extender and amplifier or preamplifiers, is significantly lower than the melt temperature $T_{m2}$ of the complex formed between the labeled probes and the amplifier. In this aspect, the assay is carried out under conditions which initially favor the formation of all hybrid complexes. The conditions are then altered during the course of the assay so as to destabilize the $T_{m1}$ hybrid complexes.

The invention additionally encompasses a method for carrying out a hybridization assay in which each of the aforementioned techniques are combined, i.e., in which nucleotidic units other than A, T, G, C, or U are incorporated into universal segments of assay components and in which the melt temperature of $T_{m1}$ hybrid complexes is significantly lower than the melt temperature of $T_{m2}$ hybrid complexes.

In a further aspect, the invention encompasses a novel method for synthesizing isoguanosine or 2'-deoxy-isoguanosine.

Finally, the invention encompasses kits containing the reagents necessary to carry out the assays described and claimed herein.

BRIEF DESCRIPTION OF THE FIGURES

FIG. 1 diagrams a solution phase sandwich hybridization assay of the prior art with heavy lines indicating the universal sequences.

FIG. 2 portrays a method for binding probes to double-stranded DNA with heavy lines indicating the universal sequences.

FIG. 3 depicts the use of non-natural nucleotide-containing probes and competimers to block non-specific hybridization.

DETAILED DESCRIPTION OF THE INVENTION

Figure 1:
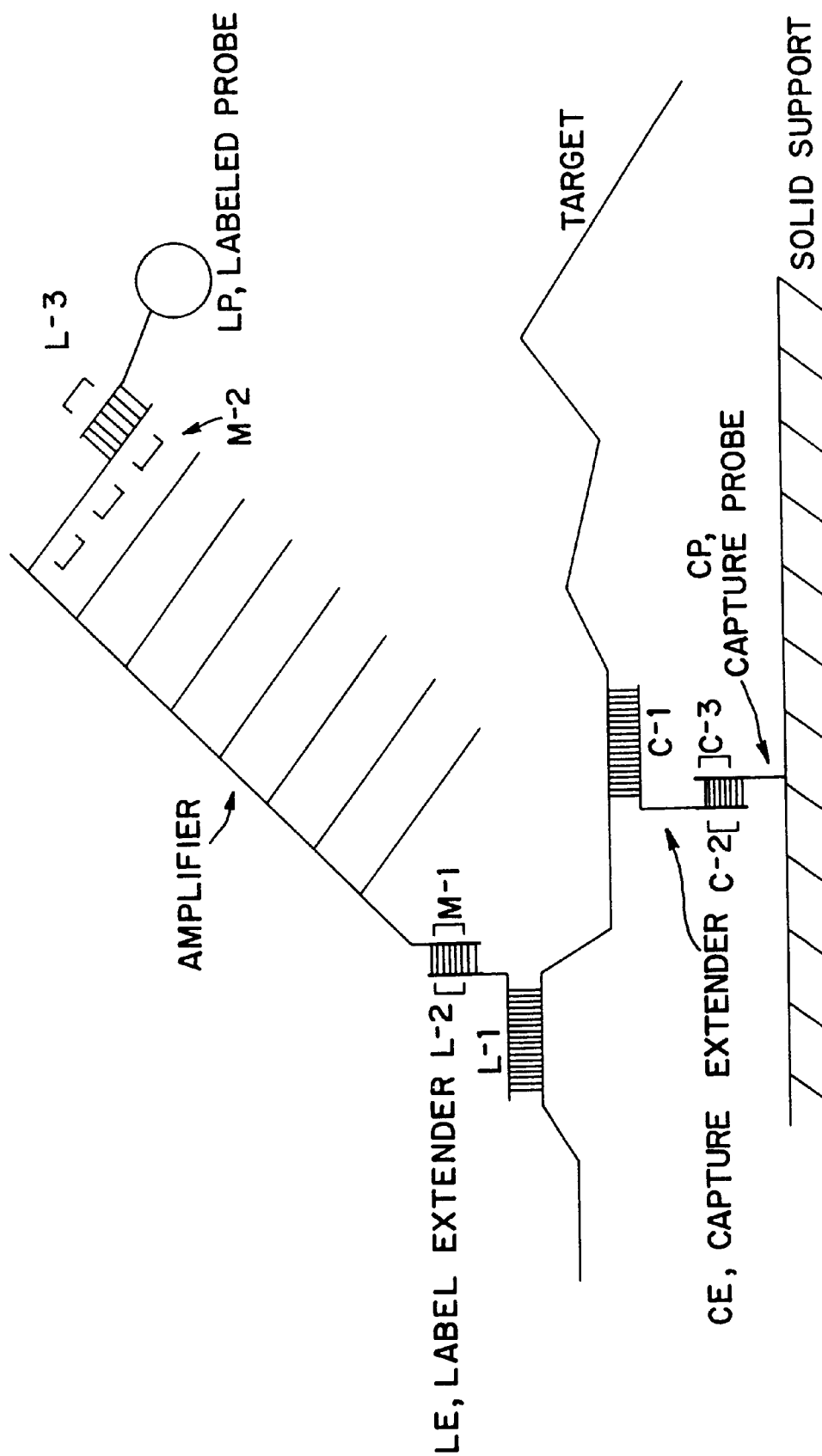
FIG. 1.

Definitions and Nomenclature:

Before the present invention is disclosed and described in detail, it is to be understood that this invention is not limited to specific assay formats, materials or reagents, as such may, of course, vary. It is also to be understood that the terminology used herein is for the purpose of describing particular embodiments only and is not intended to be limiting.

In this specification and in the claims which follow, reference will be made to a number of terms which shall be defined to have the following meanings:

As used herein, the terms "polynucleotide" and "oligonucleotide" shall be generic to polydeoxyribonucleotides (containing 2-deoxy-D-ribose), to polyribonucleotides (containing D-ribose), to any other type of polynucleotide which is an N- or C-glycoside of a purine or pyrimidine base, and to other polymers containing non-nucleotidic backbones, for example, polyamide (e.g., peptide nucleic acids (PNAs)) and polymorpholino (commercially available from the Anti-Virals, Inc., Corvallis, Oreg., as Neugene™ polymers), and other synthetic sequence-specific nucleic acid polymers providing that the polymers contain nucleobases in a configuration which allows for base pairing and base stacking, such as is found in DNA and RNA. There is no intended distinction in length between the term "polynucleotide" and "oligonucleotide," and these terms will be used interchangeably. These terms refer only to the primary structure of the molecule. Thus, these terms include double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit may form a base pair with other such modified nucleotidic units but not with A, T, C, G or U. Standard A-T and G-C base pairs form under conditions which allow the formation of hydrogen bonds between the $N^3$—H and $C^4$-oxy of thymidine and the $N^1$ and $C^6$—$NH_2$, respectively, of adenosine and between the $C^2$-oxy, $N^3$ and $C^4$—$NH_2$, of cytidine and the $C^2$—$NH_2$, $N^1$—H and $C^6$-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993), supra, and references cited therein; 2'-deoxy-5-methyl-isocytidine may be prepared by the method of Tor et al. (1993), supra, and references cited therein; and isoguanine nucleotides may be prepared using the method described by Switzer et al., supra, and Mantsch et al. (1993) *Biochem.* 14:5593–5601, or by the method described in detail below. The non-natural base pairs depicted in structure (II), referred to as κ and π, may be synthesized by the method described in Piccirilli et al. (1990) *Nature* 343:33–37 for the synthesis of 2,6-diaminopyrimidine and its complement (1-methylpyrazolo[4,3]-pyrimidine-5,7-(4H,6H)-dione. Other such modified nucleotidic units which form unique base pairs have been described in Leach et al. (1992) *J. Am. Chem. Soc.* 114:3675–3683 and Switzer et al., supra, or will be apparent to those of ordinary skill in the art.

The term "polynucleotide analyte" refers to a single- or double-stranded nucleic acid molecule which contains a target nucleotide sequence. The analyte nucleic acids may be from a variety of sources, e.g., biological fluids or solids, food stuffs, environmental materials, etc., and may be prepared for the hybridization analysis by a variety of means, e.g., proteinase K/SDS, chaotropic salts, or the like. The term "polynucleotide analyte" is used interchangeably herein with the terms "analyte," "analyte nucleic acid," "target" and "target molecule."

As used herein, the term "target region" or "target nucleotide sequence" refers to a probe binding region contained within the target molecule. The term "target sequence" refers to a sequence with which a probe will form a stable hybrid under desired conditions.

As used herein, the term "probe" refers to a structure comprised of a polynucleotide, as defined above, which contains a nucleic acid sequence complementary to a nucleic acid sequence present in the target molecule. The polynucleotide regions of probes may be composed of DNA, and/or RNA, and/or synthetic nucleotide analogs.

It will be appreciated that the binding sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "nucleic acid multimer" or "amplification multimer" are used herein to refer to a linear or branched polymer of the same repeating single-stranded oligonucleotide segment or different single-stranded polynucleotide segments, each of which contains a region where a labeled probe can bind, i.e., contains a nucleic acid sequence complementary to a nucleic acid sequence contained within a labeled probe; the oligonucleotide segments may be composed of RNA, DNA, modified nucleotides or combinations thereof. At least one of the segments has a sequence, length, and composition that permits it to bind specifically to a labeled probe; additionally, at least one of the segments has a sequence, length, and composition that permits it to bind specifically to a label extender or preamplifier. Typically, such segments will contain approximately 15 to 50, preferably 15 to 30, nucleotides, and will have a GC content in the range of about 20% to about 80%. The total number of oligonucleotide segments in the multimer will usually be in the range of about 3 to 1000, more typically in the range of about 10 to 100, and most typically about 50. The oligonucleotide segments of the multimer may be covalently linked directly to each other through phosphodiester bonds or through interposed linking agents such as nucleic acid, amino acid, carbohydrate or polyol bridges, or through other cross-linking agents that are capable of cross-linking nucleic acid or modified nucleic acid strands. Alternatively, the multimer may be comprised of oligonucleotide segments which are not covalently attached, but are bonded in some other manner, e.g., through hybridization. Such a multimer is described, for example, in U.S. Pat. No. 5,175,270 to Nilsen et al. The site(s) of linkage may be at the ends of the segment (in either normal, 3'-5' orientation or randomly oriented) and/or at one or more internal nucleotides in the strand. In linear multimers the individual segments are linked end-to-end to form a linear polymer. In one type of branched multimer three or more oligonucleotide segments emanate from a point of origin to form a branched structure. The point of origin may be another nucleotide segment or a multifunctional molecule to which at least three segments can be covalently bound. In another type, there is an oligonucleotide segment backbone with one or more pendant oligonucleotide segments. These latter-type multimers are "fork-like," "comb-like" or combination "fork-" and "comb-like" in structure, wherein "comb-like" multimers, the preferred multimers herein, are polynucleotides having a linear backbone with a multiplicity of sidechains extending from the backbone. The pendant segments will normally depend from a modified nucleotide or other organic moiety having appropriate functional groups to which oligonucleotides may be conjugated or otherwise attached. The multimer may be totally linear, totally branched, or a combination of linear and branched portions. Typically, there will be at least two branch points in the multimer, more preferably at least three, more preferably in the range of about 5 to 30, although in some embodiments there may be more. The multimer may include one or more segments of double-stranded sequences. Further information concerning multimer synthesis and specific multimer structures may be found in commonly owned U.S. Pat. No. 5,124,246 to Urdea et al.

Commonly assigned U.S. patent application Ser. No. 07/813,588 and European Patent Publication No. 541,693 describe the comb-type branched multimers which are particularly preferred in conjunction with the present method, and which are composed of a linear backbone and pendant sidechains; the backbone includes a segment that provides a specific hybridization site for analyte nucleic acid or nucleic acid bound to the analyte, whereas the pendant sidechains include iterations of a segment that provide specific hybridization sites for a labeled probe.

As noted above, a "preamplifier" molecule may also be used, which serves as a bridging moiety between the label extender molecules and the amplification multimers. In this way, more amplifier and thus more label is bound in any given target-probe complex. Preamplifier molecules may be either linear or branched, and typically contain in the range of about 30 to about 3000 nucleotides. In the preferred embodiment herein, the preamplifier molecule binds to at least two different label extender molecules, such that the overall accuracy of the assay is increased (i.e., because, again, a plurality of hybridization events are required for the probe-target complex to form).

As used herein, a "biological sample" refers to a sample of tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). Preferred uses of the present method are in detecting and/or quantitating nucleic acids as follows: (a) viral nucleic acids, such as from hepatitis B virus ("HBV"), hepatitis C virus ("HCV"), hepatitis D virus ("HDV"), human immunodeficiency virus ("HIV"), and the herpes family of viruses, including herpes zoster (chicken pox), herpes simplex virus I & II, cytomegalovirus, Epstein-Barr virus, and the recently isolated Herpes VI virus; (b) bacterial nucleic acids, such as Chlamydia, Mycobacterium tuberculosis, etc.; and (c) numerous human sequences of interest.

As used herein, the term "nonspecific hybridization" is used to refer to those occurrences in which a segment of a first polynucleotide which is intended to hybridize to a segment of a selected second polynucleotide also hybridizes to a third polynucleotide, triggering an erroneous result, i.e., giving rise to a situation where label may be detected in the absence of target molecule. The use of the term "hybridizes" is not meant to exclude non-Watson-Crick base pairing.

As used herein, the term "nonspecific binding" is used to refer to those occurrences in which a polynucleotide binds to the solid support, or other assay component, through an interaction—which may be either direct or indirect—that does not involve hydrogen bonding to support-bound polynucleotides.

Referring now to the preferred embodiment represented in FIG. 1, the following terms apply to the hybridization assay depicted therein. Note that, in FIG. 1, the universal sequences are indicated by heavy lines for clarity.

"Label extender molecules (LEs)," also referred to herein as "label extenders," contain regions of complementarity vis-à-vis the analyte polynucleotide and to the amplifying multimer ("AMP"). If a preamplifier is used (not shown in the figure), the label extender molecules will bind to this intermediate species rather than directly to the amplifier multimer. If neither preamplifier or amplifier is used, the label extender molecules will bind directly to a sequence in the labeled probe ("LP"). Thus, label extender molecules are single-stranded polynucleotide chains having a first nucleic acid sequence L-1 complementary to a sequence of the analyte polynucleotide, and a second universal region having a multimer recognition sequence L-2 complementary to a segment M-1 of label probe, amplifier multimer or preamplifier.

"Labeled probes (LPs)" are designed to bind either to the label extender, or, if an amplifier multimer is employed in the assay, to the repeating oligonucleotide segments of the multimer. LPs either contain a label or are structured so as to bind to a label. Thus, LPs contain a nucleic acid sequence L-3 complementary to a nucleic acid sequence M-2 present within the repeating oligonucleotide units of the multimer and are bound to, or structured so as to bind to, a label which provides, directly or indirectly, a detectable signal.

"Capture extender molecules (CEs)," also referred to herein as "capture extenders," bind to the analyte polynucleotide and to capture probes, which are in turn bound to a solid support. Thus, capture extender molecules are single-stranded polynucleotide chains having a first polynucleotide sequence region containing a nucleic acid sequence C-1 which is complementary to a sequence of the analyte, and a second, noncomplementary region having a capture probe recognition sequence C-2. The sequences C-1 and L-1 are nonidentical, noncomplementary sequences that are each complementary to physically distinct sequences of the analyte.

"Capture probes (CPs)" bind to the capture extenders and to a solid support. Thus, as illustrated in FIG. 1, capture probes have a nucleic acid sequence C-3 complementary to C-2 and are covalently bound to (or capable of being covalently bound to) a solid support.

Generally, solution phase hybridization assays carried out using the system illustrated in FIG. 1 proceed as follows. Single-stranded analyte nucleic acid is incubated under hybridization conditions with the capture extenders and label extenders. The resulting product is a nucleic acid complex of the analyte polynucleotide bound to the capture extenders and to the label extenders. This complex may be subsequently added under hybridizing conditions to a solid phase having the capture probes bound to the surface thereof; however, in a preferred embodiment, the initial incubation is carried out in the presence of the support-bound capture probes. The resulting product comprises the complex bound to the solid phase via the capture extender molecules and capture probes. The solid phase with bound complex is then separated from unbound materials. An amplification multimer, preferably a comb-type multimer as described above, is then optionally added to the solid phase-analyte-probe complex under hybridization conditions to permit the multimer to hybridize to the LEs; if preamplifier probes are used, the solid phase-analyte-probe complex is incubated with the preamplifier probes either along with the amplifier multimer or, preferably, prior to incubation with the amplifier multimer. The resulting solid phase complex is then separated from any unbound preamplifier and/or multimer by washing. The labeled probes are then added under conditions which permit hybridization to LEs, or, if an amplification multimer was used, to the repeating oligonucleotide segments of the multimer. The resulting solid phase labeled nucleic acid complex is then washed to remove unbound labeled oligonucleotide, and read. It should be noted that the components represented in FIG. 1 are not necessarily drawn to scale, and that the amplification multimers, if used, contain a far greater number of repeating oligonucleotide segments than shown (as explained above), each of which is designed to bind a labeled probe.

The primary focus of the present method is on eliminating the sources of background noise, by minimizing the interaction of capture probes and capture extender molecules with the labeled probes, label extender molecules and amplifiers, reducing the likelihood that incorrect moieties will bind to the support-bound capture probes.

Hybridization between complementary oligonucleotide sequences is premised on the ability of the purine and pyrimidine nucleotides contained therein to form stable base pairs. The five naturally occurring nucleotides adenosine (A), guanosine (G), thymidine (T), cytidine (C) and uridine (U) form the purine-pyrimidine base pairs G-C and A-T(U). The binding energy of the G-C base pair is greater than that of the A-T base pair due to the presence of three hydrogen-bonding moieties in the former compared with two in the latter, as shown below:

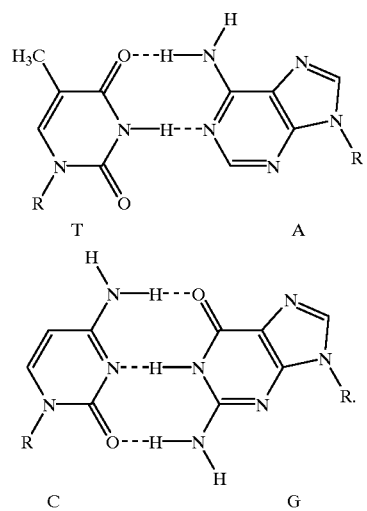

Thus, in a conventional solution phase nucleic acid sandwich assay, oligonucleotide molecules are designed to contain nucleic acid sequences which are complementary to and, therefore, hybridize with nucleic acid sequences in other assay components or in the target molecule, as explained in detail above. The method of the invention reduces nonspecific hybridization by incorporating non-natural nucleotidic units into universal oligonucleotide segments of assay components which are capable of forming unique base pairs. Furthermore, the method of the invention reduces the contribution of nonspecific binding of assay components by separating detectably labelled assay components which are associated-with the presence and/or quantity of a target analyte from those which are nonspecifically bound and contribute to assay background noise.

In a first embodiment of the invention, a hybridization assay is provided in which nucleotidic units other than A, T, C, G and U which are capable of forming unique base pairs are incorporated into hybridizing oligonucleotide segments of assay components which are not target analyte specific and thus will be less likely to form stable hybrids with target-specific probe sequences or with extraneous non-target nucleic acid sequences. Thus, as shown in FIG. 1, for example, such nucleotidic units may be incorporated in complementary nucleic acid sequences C-2/C-3, L-2/M-1 and L-3/M-2. The hybridizing oligonucleotide segments of assay components which are complementary to nucleic acid segments of the target molecule are constructed from naturally occurring nucleotides (i.e., A, T, C, G or U). Oligonucleotide segments which contain nucleotidic units may be constructed by replacing from about 15% to about 100% of the naturally occurring nucleotides with the nucleotidic unit counterpart. Preferably, every third or fourth base in an oligonucleotide will be replaced with a nucleotidic unit capable of forming a unique base pair. It will be apparent to those skilled in the art that as the percent of replacement nucleotidic units is increased, nonspecific hybridization is decreased concomitantly. However, complete replacement will require at least two new base pairs in order to maintain sufficient sequence diversity to preclude nonspecific hybridization among the universal sequences.

In another embodiment of the invention, the phenomenon of target-independent signal generation is addressed by providing a hybridization assay which is configured such that the melt temperature $T_{m1}$ of the C-2/C-3 hybrid or the L-2/M-1 hybrid is significantly lower than the melt temperature $T_{m2}$ of the L-3/M-2 hybrid. This method is premised on the design and construction of hybrid complexes such that the melt temperature $T_{m1}$ is at least about 5° C. lower than, preferably at least about 10° C. lower than, more preferably at least about 20° C. lower than the melt temperature $T_{m2}$.

This stability difference is exploited by conducting the assay under stringency conditions which initially favor the formation of $T_{m1}$ and $T_{m2}$ hybrid complexes. The stringency is altered at a subsequent step of the assay which thereby affords the physical separation of the target molecule from the capture probes or the physical separation of the amplifier-bound labeled probes from the target. Stringency can be controlled by altering a parameter which is a thermodynamic variable. Such variables are well known in the art, and include formamide concentration, salt concentration, chaotropic salt concentration, pH (hydrogen ion concentration), organic solvent content, and temperature. Preferred stringency controls are pH and salt concentration: one assay step is conducted at a pH or salt concentration which destabilizes the hybrid complex formed between capture probe/capture extender or destabilizes the hybrid formed between label extender/amplifier (or preamplifier). A preferred step at which stringency is exercised is the addition of substrate. Thus, in a preferred embodiment, the hybridization assay is conducted under conditions which favors the stability of hybrid complexes formed between all assay components and thereafter, with the addition of label substrate, the stringency is altered to destabilize hybrid complexes such as the capture probe/capture extender, or label extender/amplifier (preamplifier), and the like, with the proviso that the labeled probe is not released from the label extender or amplifier.

Another embodiment of the invention represents one means by which the above embodiment of the invention may be effected is by configuring the hybridization assay such that the complementary nucleotide sequences which form $T_{m1}$ hybrid complexes are shorter than those which form $T_{m2}$ hybrid complexes. It will be appreciated by those of skill in the art that, with shorter complementary nucleotide sequences, the opportunity for sequence diversity therein decreases. This diversity may be maintained, however, by incorporating into the complementary sequences a non-natural base pair, e.g., an isoC-isoG base pair.

It will be readily apparent to one skilled in the art that the greater the temperature difference between $T_{m1}$ and $T_{m2}$, the greater the "efficiency" of this technique in removing background noise. Thus, one skilled in the art will recognize that temperature differentials of less than 10° C., even less than 5° C., would also permit reduction of background noise, albeit to a lesser extent.

The method of the disclosed invention, whereby non-natural nucleotidic units are incorporated into hybridizing oligonucleotide sequences to increase the specificity of the hybridization with a target molecule, finds utility in a variety of applications.

In the basic or amplified solution phase nucleic acid sandwich assay, a plurality of capture probes are affixed to a solid surface. Most often, the surface area available for non-specific binding is controlled by incubating the surface with DNA from, e.g., salmon sperm or calf thymus. However, the presence of this DNA increases the potential for nonspecific hybridization of assay components to the solid support and, therefore, increased background noise. Replacement of these natural DNAs with synthetic DNAs containing non-natural bases will minimize the non-specific hybridization and the non-specific binding.

Preferably, these polynucleotides will be prepared by 3' tailing short oligonucleotides with mixtures of nucleotides by methods well known in the art. Alteratively, short, nearly random-sequence oligonucleotides containing non-natural nucleotides can be joined together to form polynucleotides. Branched DNAs can be conveniently used for this purpose. For example, the block sequence -TNVN-F-TNVN-J-TNVN-, wherein F is isoC and J is isoG, can be prepared and chemically joined to form a polymer. The advantage of using this approach over using the enzymatic 3' tailing approach is the elimination of homopolymer/homooligomer sequences.

Another application in which the construction of hybridizing oligonucleotides containing non-natural nucleotidic units finds utility is in the design of antisense compounds. Antisense compounds, as explained, for example, in Ching et al. (1989) *Proc. Natl. Acad. Sci. U.S.A.* 86:10006–10010, Broder et al. (1990) *Ann. Int. Med.* 113:604–618, Loreau et al. (1990) *FEBS Letters* 274:53–56, and PCT Publication Nos. WO91/11535, WO91/09865, WO91/04753, WO90/13641, WO91/13080 and, WO91/06629, are oligonucleotides that bind to and disable or prevent the production of the mRNA responsible for generating a particular protein. Conventional antisense molecules are generally capable of reacting with a variety of oligonucleotide species. However, due to their length (generally oligonucleotide sequences of up to 30 nucleotidic units), such antisense molecules present problems associated with nonspecific hybridization with non-target species. One solution is to use short regions of hybridization between multiple probes and the target; to strengthen the overall complex, short "dimerization domains" between the probes are used, as described by Distefano et al. (1992) *J. Am. Chem. Soc.* 114:1006–1007. The dimerization domains may be designed to have tails with complementary sequences containing non-natural nucleotidic units and thereby provide highly efficient and specific binding to the target molecule without increasing non-specific hybridization to non-target molecules. The idea is illustrated in FIG. 2 with a double-stranded DNA target.

Figure 2:
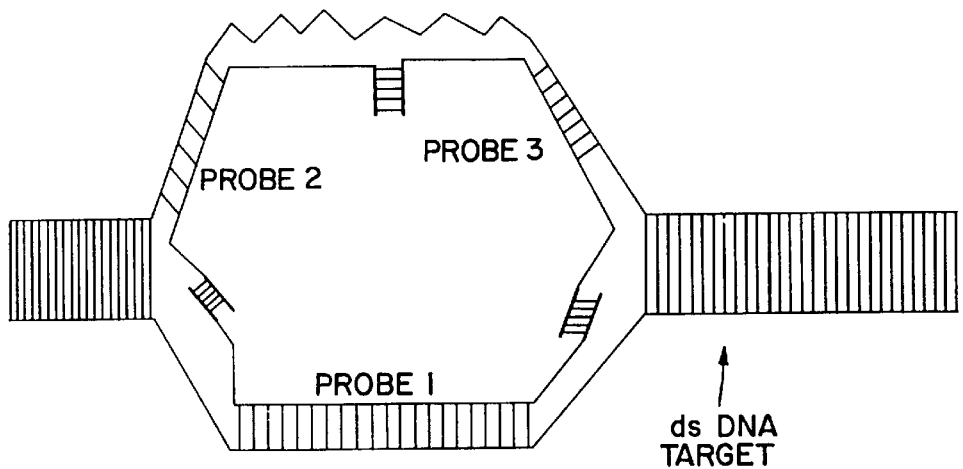
FIG. 2.

As illustrated in FIG. 2, strand displacement may be used to pry apart double-stranded DNA. AT-rich promoter sequences under superhelical stress, which are S1 nuclease-sensitive and are thus already partially single-stranded, are a particularly preferred site for this type of antigene application. Short oligonucleotides would be used to maximize specificity; their binding energy to the target would be enhanced by joining them together to form a network of oligonucleotides.

In this construct, the short universal sequences, which will not form stable base-pairs in the absence of target, contain isoc and isoG to limit nonspecific hybridization of the probes with the human sequences. Upon binding of probes 1, 2 and 3 to the target, the universal sequences will be in sufficiently close proximity that their effective concentration will be significantly increased. The universal sequences will then pair, resulting in a further increase in the strength of the binding. RNA targets may also be used in conjunction with this approach.

The SELEX procedure, described in U.S. Pat. No. 5,270, 163 to Gold et al., Tuerk et al. (1990) *Science* 249:505–510, Szostak et al. (1990) *Nature* 346:818–822 and Joyce (1989) *Gene* 82:83–87, can be used to select for RNA or DNA sequences that recognize and bind to a desired target molecule by virtue of their shape. The term "aptamer" (or nucleic acid antibody) is used herein to refer to such a single- or double-stranded DNA or a single-stranded RNA molecule. See, e.g., PCT Publication Nos. WO92/14843, WO91/19813, and WO92/05285, the disclosures of which are incorporated by reference herein. "Target molecules," as distinct from "target analytes," include polymers such as proteins, polysaccharides, oligonucletides or other macromolecules, and small molecules such as drugs, metabolites, toxins, or the like, to which an aptamer is designed to bind.

In the SELEX procedure, an oligonucleotide is constructed wherein an n-mer, preferably a randomized sequence of nucleotides thereby forming a "randomer pool" of oligonucleotides, is flanked by two polymerase chain reaction (PCR) primers. The construct is then contacted with a target molecule under conditions which favor binding of the oligonucleotides to the target molecule. Those oligonucleotides which bind the target molecule are: (a) separated from those oligonucleotides which do not bind the target molecule using conventional methods such as filtration, centrifugation, chromatography, or the like; (b) dissociated from the target molecule; and (c) amplified using conventional PCR technology to form a ligand-enriched pool of oligonucleotides. Further rounds of binding, separation, dissociation and amplification are performed until an aptamer with the desired binding affinity, specificity or both is achieved. The final aptamer sequence identified can then be prepared chemically or by in vitro transcription. When preparing such aptamers, selected base pairs are replaced with nonnatural base pairs to reduce the likelihood of the aptamers hybridizing to human nucleic acids.

One can use the present invention in at least two general ways in SELEX. First, isodG and isodC can be included among the sequences in the randomer DNA sequence pool. The number of possible randomeric structures that may recognize proteins or other important biomolecules is increased by synthesizing strands of DNA out of six or more nucleotides, rather than the conventional four nucleotide A, T, G and C. This is turn improves the chances of identifying a sequence which binds with greater affinity and/or specificity to the target molecule.

In SELEX, the conserved oligonucleotide sequences selected for may have unwanted hybridization to cellular sequences. This nonspecific hybridization can be reduced using nonnatural bases in the selection process. Nucleotides that are not recognized by human RNA and DNA polymerases but which are recognized by certain phage or bacterial polymerases are particularly useful in this application.

A second use for the instant invention in the SELEX process is in the preparation of a final aptamer construct with minimized nonspecific hybridization. For example, aptamers which display predetermined binding affinity, specificity or other target molecule recognition characteristics are selected from a pool of RNA or DNA sequences using the SELEX process. These target molecule recognition characteristics are determined by the secondary structure of the aptamer which is maintained, in part, by the formation of intramolecular oligonucleotide hybrid complexes. Upon elucidation of the secondary structure of the aptamer, it will be apparent to one of ordinary skill in the art that the specificity of base pairs in certain intramolecular hybrid complexes is highly preferred for maintaining the secondary structure and, therefore, the target molecule recognition and binding characteristics of the aptamer, i.e., there will base pairs which are preferably G-C or A-T. There will be other base pairs in these intramolecular hybrid complexes, for example, in the base-pairing portion of the stem loop, which may be replaced by any pair of complementary nucleotides, referred to herein as N-N' base pairs, without altering the secondary structure of the aptamer.

A simple replacement of selected N-N' base pairs and G-C and C-G base pairs in the final aptamer construct with isoG-isoC or isoC-isoG will reduce nonspecific hybridization to nontarget oligonucleotide sequences. Since the isoC-isoG base pair is isoenergetic with the C-G base pair, the basic shape of the molecule and the strength of the hairpins will be very similar. A base pair isoenergetic with A-U would be desirable for replacing base pairs where the winning sequences show a strong preference for A-U or U-A over C-G. These substitutions have the effect of making the aptamers more specific for the target molecule by limiting their potential for unwanted hybridization to cellular RNA and DNA sequences.

In the basic process, selected base pairs are replaced with isoC-isoG or isoG-isoC base pairs. In the final construct, isoC-isoG base pairs can comprise ribonucleotides or deoxyribonucleotides. A chimeric aptamer (composed of both ribonucleotides and deoxyribonucleotides) molecule can be made chemically. Alternatively, the ribo-isoGTP and ribo-isoCTP (with suitable 2' protection) can be used to prepare the aptamer by in vitro transcription of DNA templates containing isoC and isoG.

Other applications in which the present invention may find utility include in situ hybridizations, in reducing of nonspecific binding in hybridization assays and in polynerase chain reaction (PCR) assays.

In situ hybridization lacks sufficient sensitivity to detect a single molecule of target analyte. In situ PCR (see, e.g., Bagasra et al. (1993) *J. Immunological Methods* 158:131–145) has been developed to meet this sensitivity need; however, quantitation is not as precise with the PCR method. An alternative would use multiple label extender probes to bind the target analyte. The label extenders would bind either preamplifiers or amplifiers. If used, preamplifiers would bridge label extenders and amplifiers. The amplifiers would bind labeled probes, which would preferably be detected by luminescence (fluorescence if the sensitivity is high enough). As before, the universal sequences, L-2/M-1 and M-2/L-3 would consist of short oligonucleotides containing optimally between 15–30% isoC and isoG to reduce unwanted hybridization to human sequences. A fourth base-pair could be used to further reduce the representation of the natural bases in these sequences.

As noted earlier, nonspecific binding as well as nonspecific hybridization can be reduced by using nonnatural base pairs. Random polymers or nearly random block copolymers consisting of 6–8 different nucleotides could be used to reduce nonspecific binding of the amplifier and labeled probes to the cellular constituents that have high affinity for polynucleotides. Thus nonspecific binding will be reduced without risking an increase in nonspecific hybridization by introducing natural sequences from calf or salmon, as is commonly done.

One skilled in the art will recognize that the same strategy could be applied to blot assays, such as dot blots, Southerns, and Northerns, to reduce nonspecific hybridization and nonspecific binding of the probes to the solid supports.

The present invention also finds several uses in PCR and other exponential amplification technologies. For example, in nested PCR, after the target analyte is initially amplified and then diluted several thousand-fold, it is common to use a 5' overhang on one primer for capture and a 5' overhang on the other primer for labeling. A spacer that cannot be read by the polymerase is inserted so that the overhangs remain single-stranded (see, e.g., Newton et al. (1993) *Nucl. Acids Res.* 21:1155–1162). The generic sequences in these 5' overhangs can be prepared to contain modified base-pairs to reduce the frequency of priming on nontargets. Indeed, the presence of isodC or isodG in the first base of the 5' overhang can be used in place of the currently used spacers; the polymerase cannot read isodC or isodG because it will have no isodGTP or isodCTP to put in place of it. Because the polymerase may put T into the polymer at a low frequency when it detects isodG in what was the primer, it is preferable to use isoC as the first base in the 5' overhang.

EXPERIMENTAL

The practice of the present invention will employ, unless otherwise indicated, conventional techniques of synthetic organic chemistry, biochemistry, molecular biology, and the like, which are within the skill of the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait, ed., 1984); *Nucleic Acid Hybridization* (B. D. Hames & S. J. Higgins, eds., 1984); and the series, *Methods in Enzymology* (Academic Press, Inc.).

All patents, patent applications, and publications mentioned herein, both supra and infra, are hereby incorporated by reference.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Temperature is always given in degrees C and, unless otherwise indicated, pressure is at or near atmospheric.

Synthesis of Isoguanosine or 2'-Deoxy-isoguanosine

Few procedures have been reported for the synthesis of isoguanosine or 2'-deoxy-isoguanosine. For example, 2'-deoxy-isoguanosine has been synthesized: 1) from 2'-deoxyadenosine via 2'-deoxyadenosine-($N^1$-oxide) by direct photolysis under basic conditions (Switzer et al. (1993), supra); 2) from 2-chloro-2'-deoxyadenosine by direct photolysis under basic conditions (Seela et al. (1992) *Helv. Chim. Acta* 75:2298–2306); and 3) by a chemical route from 6-amino-1-(2'-deoxy-beta-D-erythropentofuranosyl)-1H-imidazole-4-carbonitrile [AICA 2'-deoxynucleoside], which was reacted with benzoyl isocyanate followed by treatment with ammonia to affect annealation of the pyrimidine ring (Kazimierczuk et al. (1991) *Helv. Chim. Acta* 74:1742–1748).

However, because the photolytic conversion of 2'-deoxyadenosine-($N^1$-oxide) to 2'-deoxy-isoguanosine does not lend itself readily to scale-up, a convenient, chemical route to 2'-deoxy-isoguanosine from readily available 2'-deoxyribonucleoside starting materials was developed.

Several procedures for the conversion of 2'-deoxyguanosine into 2,6-diaminopurine nucleoside and $N^6$-alkyl-2,6-diaminopurine nucleoside via special "convertible" 2'-deoxyguanosine derivatives, such as $O^6$-phenyl-2'-deoxyguanosine, have been described (MacMillan et al. (1991) *Tetrahedron* 47:2603–2616; Gao et al. (1992) *J. Org. Chem.* 57:6954–6959; and Xu et al. (1992) *Tetrahedron* 48:1729–1740). Further, Fathi et al. (1990) *Tetrahedron Letters* 31:319–322 described a convenient synthesis of $O^6$-phenyl-2'-deoxyguanosine using a procedure involving treatment of 2'-deoxyguanosine with trifluoroacetic anhydride/pyridine followed by in situ displacement with phenol. Alternatively, the introduction of $O^6$-phenyl moieties into 2'-deoxyguanosine has been described by Reese et al. (1984) *J. Chem. Soc., Perkin Trans. I*, 1263–1271, where the intermediate $O^6$-(4-toluenesulfonyl)-2'-deoxyguanosine was treated with trimethylamine followed by phenol to affect displacement of $O^6$-(4-toluenesulfonyl) to give $O^6$-phenyl-2'-deoxyguanosine. An isoguanosine-like compound was generated from 2-(methylmercapto)-6-amino-pyrazolopyrimidine ribonucleoside by S-oxidation, producing 2-(methylsulfonyl)-6-amino-pyrazolopyrimidine ribonucleoside, followed by displacement with NaOH to give the isoguanosine analogue (Cottam et al. (1983) *Nucleic Acids Research* 11:871–882).

Transformation of the 2-amino group in guanosine and 2'-deoxyguanosine using alkyl nitrites have been described. These include conversion to 2-halo (Nair et al.(1982) *Synthesis* 670–672), and 2-(methylmercapto)-6-chloro-purine ribonucleoside (Trivedi (1991) in *Nucleic Acid Chemistry*, Townsend et al. (eds.) Wiley Inter-Science, Part 4, 269–273), in radical-reactions. Oxidation of $O^6$-(p-nitrophenylethyl)-3',5'-O-di-t-butyl-dimethyl silane-2'-deoxyguanosine with neat pentyl nitrite to yield $O^6$-(p-nitrophenylethyl)-3',5'-O-di-TBDMS-2'-deoxyxantosine has been reported (Steinbrecher et al. (1993) *Angew. Chem. Int. Ed. Engl.* 32:404–406).

A procedure for the synthesis of 2'-deoxy-isoguanosine has been described in Seela et al. (1994) *Helv. Chim. Acta* 77:622–30. In a first step, 2'-deoxyguanosine was converted to 2-amino-2'-deoxyadenosine. In a second step, 2-amino-2'-deoxyadenosine was deaminated by diazotization of the 2-amino group with sodium nitrite to give 2'-deoxy-isoguanosine.

The method disclosed and claimed herein for synthesizing a compound having the structural formula

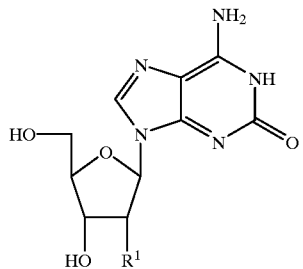

wherein $R^1$ is selected from the group consisting of hydrogen, hydroxyl, sulfhydryl, halogeno, amino, alkyl, allyl and —$OR^2$, where $R^2$ is alkyl, allyl, silyl or phosphate, comprises:
a) reacting a compound having the structural formula

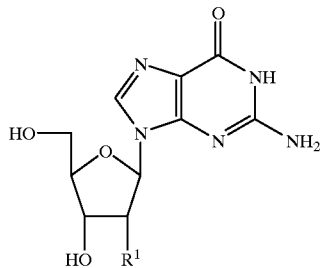

with a reagent suitable to protect both the 3' and 5' hydroxyl groups;
b) reacting the product of step (a) with a reagent suitable to convert the $O^6$-oxy moiety into a functional group which is susceptible to nucleophilic displacement, thereby producing a functionalized $O^6$ moiety;
c) oxidizing the 2-amino group of the product of step (b);
d) reacting the product of step (c) with a nucleophilic reagent to displace the functionalized $O^6$ moiety; and
e) reacting the product of step (d) with a reagent suitable to deprotect the protected 3' and 5' hydroxyl groups.

The conversion of guanosine or 2'-deoxyguanosine to isoguanosine or 2'-deoxy-isoguanosine, respectively, may be effected by protecting the hydroxyl groups on the sugar moiety using a suitable reagent, e.g., TBDMS, benzoyl chloride, acetic anhydride, or the like. As previously noted, one or more of the hydroxyl groups on the sugar moiety may be replaced by halogen, aliphatic groups, or may be functionalized as ethers, amines, or the like. The product is isolated and the $O^6$ is modified such that it can be displaced by a suitable nucleophile. Examples of such displaceable groups include, for example, $CH_3$—S—$C_6H_4$—$O^6$—, $C_6H_5$—$SO_2$—$O^6$—, $C_6H_5$—$O^6$—, 4-nitro-$C_6H_4$—$O^6$—, 2,4,6-trinitro-$C_6H_2$—$O^6$—, or the like. The 2-amino group is then transformed to the oxy function using an alkyl nitrite, or other suitable agent as known in the art (see, Nair et al. (1982), supra; Trevidi (1991), supra; or Steinbrecher et al. (1993), supra). The product is reacted with a suitable nucleophile, e.g., $KH_4OH$, or other aminoalkyl, aminoaryl, aminoheteroalkyl, aminoheteroaryl containing a terminal —$NH_2$, —SH, —COOH, or the like, thereby displacing the modified $O^6$ leaving group. Deprotection of the protected hydroxyl groups may be effected by treatment with, for example, base or fluoride.

In the following discussion, $O^6$-(4-methylthiophenyl) will serve as an exemplary displaceable group. However, its use is for the purpose of describing particular embodiments only and is not-intended to be limiting.

$N^6$-alkylated isoguanosine derivatives can be readily synthesized by using an alkyl amine as the nucleophile. For example, hexanediamine may be used to displace the $O^6$-(4-methylthiophenyl) to form $N^6$-(6-10 aminohexyl)-isoguanosine. Protection of the aminohexyl group (e.g., as the trifluoroacetamido derivative) and subsequent conversion into a phosphoramidite reagent provides a functionalizable isoguanosine analog which may be incorporated in any desired position in an oligonucleotide for further post-synthesis derivatization. Thus, it would be possible to label specifically the isoguanosine moiety of selected isoguanosine/isocytidine base pairs. It would also be possible to synthesize a series of $N^6$-derivatives of isoguanosine which carry any desired functionality simply by displacing the $O^6$-(4-methylthiophenyl) group with a suitably terminated nucleophile, e.g., —COOH, —SH, —$NH_2$, or the like, derivatives can be readily prepared.

Furthermore, $O^2$-(4-methylthiophenyl)-2'-deoxyxantosine, in its fully protected phosphoramidite form ($O^2$-(4-methylthiophenyl)-5'-O-DMT-3'O-(BCE-diisopropylphosphoramidite)-2'-deoxyxantosine) may be used as a convertible derivative following incorporation into an oligonucleotide. Post-synthesis displacement of the $O^2$-(4-methylthiophenyl) from the $O^2$-(4-methylthiophenyl)-2'-deoxyxantosine with an alkyldiamine, or other functionalized alkyl amine, produces $N^6$-(aminoalkyl)-2'-deoxy-isoguanosine-containing oligonucleotides. The derivatized isoguanosine can serve as a site for introduction of a label or other reporter molecule specifically at the functionalized isoguanosine residue.

Outline of Synthetic Approach. As depicted in Scheme 1, the synthesis of 2'-deoxy-isoguanosine was accomplished in five steps from 2'-deoxyguanosine as follows:

1) conversion of 2'-deoxyguanosine to 3',5'-O-(t-butyldimethylsilyl)$_2$-2'-deoxyguanosine (Ogilvie et al. (1973) Can. J. Chem. 51:3799–3807), with purification by recrystallization;
2) conversion to $O^6$-(4-toluenesulfonyl)-3',5'-O-TBDMS$_2$-2'-deoxyguanosine;
3) displacement of 4-toluenesulfonyl group at $O^6$ with a suitable phenol, e.g., 4-(methylthio)phenol or phentachlorophenyl, using Reese's procedure to give $O^6$-(4-(methylthio)phenyl)-3',5'-O-TBDMS$_2$-2'-deoxyguanosine (Reese et al. (1984), supra);
4) oxidation of the 2-amino group to the oxy function with tert-butyl nitrite under neutral conditions to give $O^6$-(4-(methylthio)phenyl)-3',5'-O-TBDMS$_2$-2'-deoxyxantosine (Steinbrecher et al. (1993), supra); and
5) displacement of $O^2$-(4-methylthiophenyl) group with ammonium hydroxide at elevated temperature to give 3',5'-O-TBDMS$_2$-2'-deoxy-isoguanosine.

The synthesis of isoguanosine from guanosine may be effected using a similar reaction scheme.

SCHEME 1
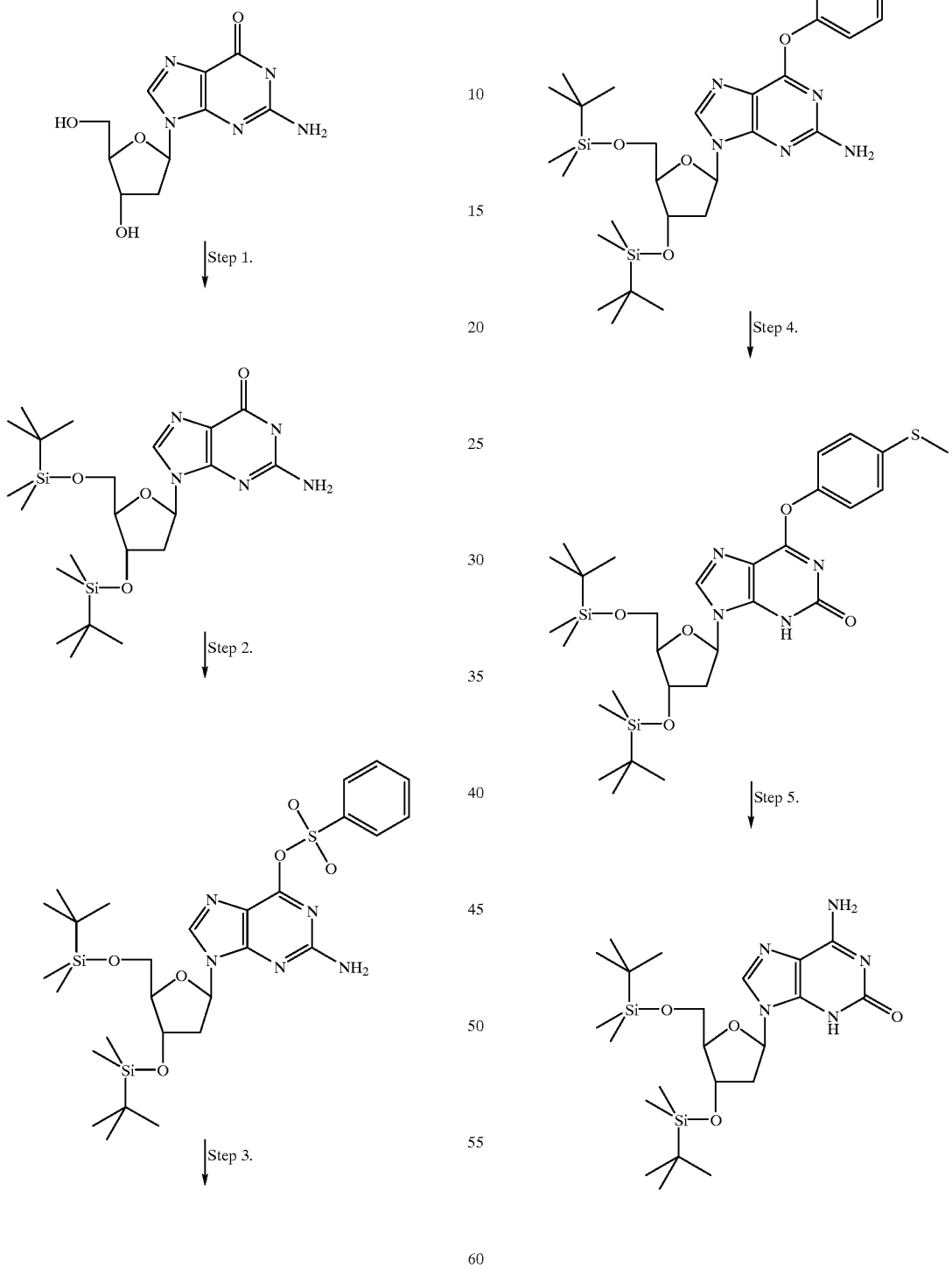

The material obtained was identical in every respect (TLC, HPLC, UV, and NMR) to an authentic sample prepared by a published, photolytic route (Switzer et al. (1993), supra).

Preparation of Isocytidine or 2'-Deoxy-isocytidine Derivatives

Derivatives of isocytidine or 2'-deoxy-isocytidine may be prepared in which the glycosidic bond is stabilized against exposure to dilute acid during oligonucleotide synthesis. $N^2$-amidine derivatives have been described for 2'-deoxyadenosine by, for example, McBride et al. (1986) *J. Am. Chem. Soc.* 108:2040–2048, Froehler et al. (1983) *Nucleic Acids Res.* 11:8031–8036 and Pudlo et al. (1994) *Biorg. Med. Chem. Lett.* 4:1025–1028. $N^2$-(N,N-di(X) formamidino)-2'-deoxy-isocytidine was synthesized by the following procedure. As exemplified herein, X is n-butyl. However, X may be $C_2$–$C_{10}$ alkyl, aryl, heteroalkyl, heteroalkyl, or the like.

N-di-n-butylformamide dimethylacetal was synthesized by transamination of N,N-methylformamide dimethylacetal with di-n-butylamine as described in McBride et al. (1986), supra, Froehler et al. (1983), supra, and Pudlo et al. (1994), supra. Ten mmole of 2'-deoxy-5-methyl-isocytidine was suspended in 100 ml methanol and 10 mmole of N,N-di-n-butylformamide dimethylacetal was added. After 2 hours at room temperature with stirring, a clear solution resulted. Thin layer chromatography analysis on silica 60H developed using 10% methanol in methylene chloride indicated that the starting material was completely consumed. Water (10 ml) was added to destroy excess reagent, and the solvents were removed in vacuo to give 3.8 grams of crude $N^2$-(N,N-dibutylformamidino)-2'-deoxy-isocytidine. This derivative can be directly converted to 5'-O-DMT-$N^2$-(N,N-dibutylformamidino)-2'-deoxy-isocytidine for incorporation into oligonucleotides.

Other isocytidine derivatives may be prepared which provide functionalizable substituents by which detectable labels may be incorporated into a specific position of an oligonucleotide. For example, 5-alkylated 2'-deoxyuridine derivatives have been described, e.g., 5-[N-(6-trifluoroacetylaminohexyl)-3-(E)acrylamido]-2'-deoxyuridine, by Ruth (1991) *Oligodeoxynucleotides with Reporter Groups Attached to the Base*, in Eckstein (ed.) *Oligonucleotides and Analogues*, IRL press, p. 255–282. Such 5-position derivatives have been found not to obstruct base pair hybridization patterns. The chemistry described by Ruth can be used to synthesize 5-[N-(6-trifluoroacetylaminohexyl)-3-(E)acrylamido]-2'-deoxy-isocytidine, thereby providing a functionalized isocytidine which may be detectably labelled at selected isoguanosine*isocytidine base pairs.

These and other 5-position derivatives of isocytidine and 2'-deoxy-isocytidine provide additional stabilization for base pair formation. Such derivatives include: 5-β-propynyl (see, Froehler et al. (1993) *Tetrahedron Lett.* 34:1003–1006), 5-β-propenyl or other 5-alkyl isocytidine or 2'-deoxy-isocytidine derivatives.

Kits for carrying out nucleic acid hybridization assays according to the invention will comprise in packaged combination at least one hybridizing oligonucleotide probe, a segment of which is capable of forming a hybrid complex with the analyte, and a means for detecting the hybrid complex, wherein the at least one hybridizing oligonucleotide probe comprises a first nucleotidic unit which, under conditions in which A-T and G-C base pairs are formed, will not effectively base pair with adenosine (A), thymidine (T), cytidine (C), guanosine (G) or uridine (U). The reagents will typically be in separate containers in the kit. The kit may also include a denaturation reagent for denaturing the analyte, hybridization buffers, wash solutions, enzyme substrates, negative and positive controls and written instructions for carrying out the assay.

The polynucleotides of the invention may be assembled using a combination of solid phase direct oligonucleotide synthesis, enzymatic ligation methods, and solution phase chemical synthesis as described in detail in commonly assigned U.S. patent application Ser. No. 07/813,588.

All chemical syntheses of oligonucleotides can be performed on an automatic DNA synthesizer (Perkin Elmer/Applied Biosystems Division model 380 B). Phosphoramidite chemistry of the β-cyanoethyl type was used including 5'-phosphorylation which employed PHOSTEL™ reagent (DMT-O—$CH_2CH_2$—($SO_2$)—$CH_2CH_2$—O—P(N(iPr)$_2$) (—O—$CH_2CH_2$CN) wherein DMT is dimethoxytrityl and iPr is isopropyl). Standard manufacturer's protocols were used unless otherwise indicated.

Example 1

Assay Background Noise Caused by Nonspecific Hybridization of Target-Specific Extender Sequences with Generic Assay Components In order to determine how assay background noise can be caused by cross-hybridization of target-specific extender sequences with generic assay components, an amplified DNA hybridization assay was performed to quantitate M13 phage using the pools of capture extenders and label extenders as shown in Tables 1, 2 and 3.

TABLE 1

| SEQ ID NO: | Capture Extender Pool A |
|---|---|
| 1 | ATTGCGAATAATAATTTTTTCACGTTGAAAATC TTCTCTTGGAAAGAAAGTGAT |
| 2 | GAATTTCTTAAACAGCTTGATACCGATAGTTG TTCTCTTGGAAAGAAAGTGAT |
| 3 | ATTGTATCGGTTTATCAGCTTGCTTTCGAGGT TTCTCTTGGAAAGAAAGTGAT |
| 4 | CCGCTTTTGCGGGATCGTCACCTTCTC TTGGAAAGAAAGTGAT |
| 5 | GCTGAGGCTTGCAGGGAGTTAAAGG TTCTCTTGGAAAGAAAGTGAT |

TABLE 1-continued

| SEQ ID NO: | Capture Extender Pool A |
|---|---|
| 6 | ATGAGGAAGTTTCCATTAAACGGGT TTCTCTTGGAAAGAAAGTGAT |
| 7 | TCGCCTGATAAATTGTGTCGAAATCC TTCTCTTGGAAAGAAAGTGAT |

TABLE 2

| SEQ ID NO: | Capture Extender Pool B |
|---|---|
| 8 | TCCAAAAAAAAAGGCTCCAAAAGGAGCCTTTA TTCTCTTGGAAAGAAAGTGAT |
| 9 | CGCCGACAATGACAACAACCATCGC TTCTCTTGGAAAGAAAGTGAT |

TABLE 3

| SEQ ID NO: | Label Extender Pool |
|---|---|
| 10 | ATGAGGAAGTTTCCATTAAACGGGT TTAGGCATAGGACCCGTGTCT |
| 11 | GAGGCTTTGAGGACTAAAGACTTTTTC TTAGGCATAGGACCCGTGTCT |
| 12 | CCCAGCGATTATACCAAGCGCG TTAGGCATAGGACCCGTGTCT |
| 13 | AAGAATACACTAAAACACTCATCTTTGACC TTAGGCATAGGACCCGTGTCT |
| 14 | CTTTGAAAGAGGACAGATGAACGGTG TTAGGCATAGGACCCGTGTCT |
| 15 | GGAACGAGGCGCAGACGGTCA TTAGGCATAGGACCCGTGTCT |
| 16 | ACGAGGGTAGCAACGGCTACA TTAGGCATAGGACCCGTGTCT |
| 17 | GCGACCTGCTCCATGTTACTTAGCC TTAGGCATAGGACCCGTGTCT |
| 18 | CTCAGCAGCGAAAGACAGCATCGGA TTAGGCATAGGACCCGTGTCT |
| 19 | ATCATAAGGGAACCGAACTGACCAA TTAGGCATAGGACCCGTGTCT |
| 20 | CCACGCATAACCGATATATTCGGTC TTAGGCATAGGACCCGTGTCT |
| 21 | TACAGACCAGGCGCATAGGCTGGC TTAGGCATAGGACCCGTGTCT |
| 22 | AAACAAAGTACAACGGAGATTTGTATCA TTAGGCATAGGACCCGTGTCT |
| 23 | CACCAACCTAAAACGAAAGAGGCGA TTAGGCATAGGACCCGTGTCT |
| 24 | AAAATACGTAATGCCACTACGAAGG TTAGGCATAGGACCCGTGTCT |

For the purpose of illustration, a space separates the 3' nontarget binding region from the target-binding region of each probe.

The assay was run essentially as described in copending application Ser. No. 08/164,388 (Urdea et al). Briefly, after overnight hybridization at 63° C. in microtiter wells containing capture probes complementary to the nontarget binding region of the capture extenders, the plates were cooled at room temperature for 10 min, washed twice with a buffer containing 0.1×SSC (15 mM NaCl; 1.5 mM sodium citrate; pH 7.0), 0.1% sodium dodecyl sulfate. A 15×3 (15 "arms" each with 3 alkaline phosphatase probe binding sites) branched DNA amplifier (100 fm) complementary to the 3' nontarget binding region of the label extender was added to the wells and the incubation was continued for 30 min at 53° C. after which the plates were cooled and washed as above. After the addition of an alkaline phosphatase probe (200 fm) to the wells and a further incubation for 15 min at 53° C., the plates were again cooled and washed as above. Three additional washes were done with a 0.1×SSC buffer. The signals were detected in a Chiron luminometer after 20 min in the dioxetane phosphate substrate solution Lumiphos 530 (Lumigen). The results are shown in Table 4.

TABLE 4

Nonspecific Binding Assay Background Noise

| Capture Extender Pool | Signal (+ M13 phage) | Noise (− M13 phage) |
|---|---|---|
| Pool A alone | 293, 306, 337, 359 | 1.1, 0.9, 1.1, 2.0 |
| Pool A + Pool B | 390, 393, 379, 376 | 103, 130, 436, 172 |

The addition of the pool B capture extenders does not increase the net signal, but does increase the noise about one hundred-fold. Computer analysis of the sequences involved showed that capture extender #8 of pool B has extensive homology with the T20—LLA2 sequence of the branched DNA amplifier (including a 9 mer oligo(dA)—oligo(dT)), while capture extender #9 of pool B has extensive homology with the BLA3c sequence of the branched DNA amplifier.

The present invention addresses the problem of hybridization-dependent assay background noise. Nucleotide sequences are constructed which are interrupted by nucleotides that do not form stable base pairs with "natural" nucleobases, thereby inhibiting the hybridization of such sequences with natural sequences. Ideally, every third or fourth base in the universal sequence would be a modified nucleotide that does not pair with A,C, G, or T(U). By using base pairs isoenergetic with the C*G base pair, one can also reduce the length of the universal sequences. Statistical arguments show that this should also reduce the frequency of undesirable cross-hybridization among universal sequences and between universal sequences and nontarget sequences in the sample and between universal sequences and the target-specific sequences in the extender probes. By relying on multidentate binding to form stable hybrids, the lengths of the universal sequences can be further reduced (see copending application Ser. No. 08/164,338). All universal sequences would be designed with at least 6 and preferably 8 nucleotides: capture probe, capture extender tails, label extender tails, amplifiers, labeled probes, and preamplifiers (when applicable).

Example 2

Specificity and Strength of isoC-isoG Base Pairs

In order to determine the specificity and strength of the isoC-isoG base pair, thermal melt analysis was done on the following oligonucleotides:
1) 5' (L) CA CCA CTT TCT CC (T) 3' [SEQ ID NO: 25];
2) 5' (L) CA CFA CTT TCT CC (T) 3' [SEQ ID NO: 26];
3) 3' (T) GT GGT GAA AGA GG 5' [SEQ ID NO: 27];
4) 3' (T) GT GJT GAA AGA GG 5' [SEQ ID NO: 28]; and
5) 5' CA CTA CTT TCT CC (T) 3' [SEQ ID NO: 29].

The core hybrid of these oligonucleotides consists of thirteen nucleotides. Nucleotides not involved in the base-pairing are indicated in parentheses. L=a primary amine, F=isoC, J=isoG. Thermal melt analysis was done on a Cary 3E Spectrophotometer in 3×SSC (0.45 M NaCl, 0.045 M sodium citrate), pH 7.9. Each of the two oligonucleotides incubated together was present at approximately 1.5 μM. The $T_m$ was calculated as the maximum in a plot of $dA_{260}/dT$ vs temperature. The results shown in Table 4 indicate that the isoC*isoG base pair is isoenergetic with the natural C*G base pair.

TABLE 4

$T_m$ Analysis of Specificity of isoC*isoG Base-pairing

| Match/Mismatch, Paired Oligonucleotides | $T_{m1}$ | $T_{m2}$ | Avg $T_m$ |
|---|---|---|---|
| C * G match, 1*3 | 60 | 60 | 60 |
| isoC * isoG match, 2*4 | 60 | 61 | 60 |
| isoC * G mismatch, 2*3 | 52 | 52 | 52 |
| isoG * C mismatch, 1*4 | 52 | 52 | 52 |
| G * T mismatch, 3*5 | 50 | 49 | 49 |
| isoG * T mismatch, 4*5 | 53 | 53 | 53 |

Accordingly, universal sequences containing approximately equimolar C, G, isoC, isoG, A, and T, can be shorter than sequences containing only A, T, C, G in approximately equal ratios. This limits the potential for cross-reactivity with natural nontarget sequences in the sample and with LE and CE target-binding sequences that are more or less constrained to be composed of A, T(U), C, and G.

The data also show the specificity of the isoC*isoG base-pair. The isoC*G and isoG*C pairs behave as mismatches. Classically, the destabilization in degrees C is approximated by the percent mismatching. Thus, about a 7.5° C. change in $T_m$ would be predicted to occur for 1 mismatch in 13 nucleotides (7.5% mismatch). The observed 8° C. change when the C*G or isoC*isoG matches are compared with the mismatches is similar to the change which would occur in an average mismatch with A, T, C, and G code.

IsoG exists in at least two tautomeric forms, the keto and the enol. The keto form is favored in aqueous solvents and the enol is favored in organic solvents (Sepiol et al. (1976) Zeitschrift fuer Naturforschung 31C:361–370). The isoG enol tautomer can, in principle, form two hydrogen bonds to dT, making it analogous to the A*T base pair. If the enol tautomer were present at significant levels in the hybridization buffer, the specificity of isoC*isoG base pair would be limited. However, the observed $T_m$ in the isoG*T mismatch was 53° C., essentially the same as the other mismatches.

These data support the conclusion that the enol tautomer is present at very low concentration in 3×SSC at pH 7.9 or, if present, it still forms a hybrid with 7–8° C. lower $T_m$ than the isoC-isoG hybrid. The control with a G*T mismatch had a $T_m$ of about 49° C. This is somewhat lower than expected for the average G*T mispair, but is close to the isoG-T mispair.

One skilled in the art will appreciate that having still another base-pairing combination (i.e., 8 bases, 4 pairs), whether isoenergetic with C*G or not, would further improve the specificity of the base-pairing among universal sequences. In this case, one could nearly eliminate A, T, C, and G from the universal sequences. However, having a small representation of these bases adds to the diversity of the library of possible universal sequences, which enables one to design universal sequences that are as noninteracting as possible among themselves.

For example, with a 4 base code one can design only two pairs of universal 15 mers that do not have even a single 3 mer cross hybrid. That is, with the addition of a third pair of 15 mer sequences, there must be at least some 3 nucleotide cross hybrids. With a six base code, one can design 8 pairs of 15 mer sequences without even one 3 mer Watson-Crick type of cross-hybrid. With an eight base code, one can design 19 such pairs of 15 mers.

Example 3

The Effect of pH on isoC*isoG Base Pairing

In order to examine the behavior of the isoC*isoG base pair as a function of pH, $T_m$ analysis was conducted on the oligonucleotides provided in Example 2. The effect of pH on the $T_m$ of the oligonucleotides containing the complementary isoC*isoG base pair (sequences 2 and 4, respectively) and C*G base pair (sequences 1 and 3, respectively) was determined (n=2 or 3) at 0.5 M salt and approximately 1.5 μM oligonucleotide, and the results are shown in Table 5.

TABLE 5

$T_m$ Analysis of pH-sensitivity of isoC*isoG Base Pair

| Hybrid, Paired Oligonucleotides | pH | $T_{m1}$ | $T_{m2}$ | $T_{m3}$ | Avg $T_m$ |
|---|---|---|---|---|---|
| isoG*isoC, 2*4 | 7.9 | 62 | 60 | 62 | 61 |
| isoG*isoC, 2*4 | 5.1 | 60 | 59 | 60 | 60 |
| isoG*isoC, 2*4 | 9.5 | 53 | 51 | 52 | 52 |
| G*C, 1*3 | 9.5 | 52 | 52 |  | 52 |

Generally, oligonucleotide hybrids are stable at pH 5 and pH 10. Below pH 5, C and A become protonated, while above pH 10, G and T begin to lose their imino protons. Thus, below pH 5 and above pH 10, nucleic acid hybrids show reduced stability. The data of Table 2 show that the isoC*isoG base pair has normal acid stability. However, both the isoG*isoC hybrid and the G*C hybrid show an unusual −9° C. change in $T_m$ over a 1.6 unit pH increase. This is probably due to their very short length.

Theoretically, one could select hybrids with still greater pH-sensitivity using the SELEX protocol, described in U.S. Pat. No. 5,270,163 to Gold et al., Tuerk et al. (1990) *Science* 249:505–510, Szostak et al. (1990) *Nature* 346:818–822 and Joyce (1989) *Gene* 82:83–87, in which a population of DNA or RNA randomers would be selected for binding at neutral pH and for dissociation from the target sequence at mildly alkaline or mildly acid pH. Following amplification, the selection process would be iteratively repeated. After the final iteration, those oligomers which show the desired pH sensitivity would be cloned and sequenced. Those sequences would be synthesized and the best performers selected in a direct competition assay.

Lability in mild base can be exploited in the current amplified DNA assay format to reduce assay background noise. In the final step, the substrate buffer used is typically pH 9.5 to 10.5. With a capture probe with the proper base lability, the target will come off the surface and could be detected in another well. The background will be left behind. Minimization of capture extender binding to the support by the methods disclosed in copending application Ser. No. 08/164,388 (Urdea et al.) will reduce background noise caused by release of molecules nonspecifically bound to capture probes through capture extenders.

Since one would not want to release alkaline phosphatase probes hybridized to nonspecifically bound amplifiers, preferably the capture probe-capture extender hybrids would be selected to have considerably more base lability (i.e., higher $T_m$ at a given pH) than the amplifier and labeled probe and the amplifier and label extender hybrids. Alternatively, L-2/M-2 hybrid of FIG. 1 could be the base-labile hybrid. In either instance, the M-2/L-3 hybrid must be the most stable; otherwise, labeled probe hybridized to nonspecifically bound amplifier would be released.

As noted above, one could also conceivably transfer the released target to fresh wells for reading. However, it would be preferable to read the released solution in the well where it was generated. This would avoid additional pipetting steps and eliminate imprecision associated with additional liquid transfer steps. There are several methods by which well transfers may be avoided, as described below.

To further enhance the specificity of the assay, the specific release of the target could be coupled with masking the background on the surface. In this case, the transfer to another support would be unnecessary. For example, the surface of the solid support could be coated with inhibitors of the labeled probe and/or various luminescence inhibitors, absorbers, or quenchers. One surface coating currently in use is poly(phe-lys). Phenylalanine is a known inhibitor of alkaline phosphatase, a particularly preferred enzyme label. One could include in the polymeric peptide coating other inhibitors of alkaline phosphatase such as tryptophan and cysteine. Examples of luminescent inhibitors include compounds with low quantum yields, i.e., any compound that preferentially gives off heat rather than light after being excited by collision with a dephosphorylated dioxetane.

There are at least two other convenient ways to make detection of the released solution more selective to avoid transfer of the released target to another well. The target-associated signals can be read in solution by making the solid phase inaccessible to visualization reagents or by masking signal generating reactions which occur on the solid support. Isolating the solid phase from subsequent visualization steps could be done by adding a heavier-than-water immiscible oil to the reaction vessel. This oil would cover the bottom of the vessel while allowing the solution of interest to float to the top. For simple calorimetric detection by visual or by reflectance measurement, an opaque substance could be added to the oil to serve as a neutral background for visualization.

For chemiluminescent detection the oil could be filled with an optically opaque substance. If a white solid such as titanium dioxide were used, light emitted from the floating aqueous layer would be reflected upward out of the container for detection. A dark solid or dye molecule dissolved in the oil could also be used to mask the stationary phase. Even if the oil solution does not completely isolate the solid phase from visualization reagents, the suspended solids or dissolved dyes would block the transmission of this light from the surface.

It is also possible that a stationary phase could be colored with a dye that would block emission of light from reactions that occur near its surface. This would be particularly convenient with a colored bead as a solid phase contained within an opaque well.

Example 4

The Effect of Salt on isoC*isoG Base Pair at Neutral and Alkaline pH

In order to examine the behavior of the isoC*isoG base pair as a function of salt concentration, $T_m$ analysis was conducted of the oligonucleotides provided in Example 2. The effect of salt concentration on the $T_m$ of the oligonucleotides containing the complementary isoC*isoG base pair (sequences 2 and 4, respectively) and C*G base pair (sequences 1 and 3, respectively) was determined (n=3) at pH 7.9 or 9.5 and approximately 1.5 μM oligonucleotide, and the results are shown in Table 6.

Classically, polynucleotides show a change of approximately 16–17° C. in $T_m$ for each log change in salt concentration. Oligonucleotides often show somewhat reduced salt dependence. The 10–11° C. change in $T_m$ per log change in salt at pH 7.9 calculated for the isoC*isoG hybrid approximates what would be expected for a 13 mer. However, the change at pH 9.5 of only about 3° C. for the isoC*isoG hybrid and 5 degrees for the C*G hybrid per log change in salt was surprisingly low.

This can be also exploited in a specific release of target. Generally, low salt is used for specific release of target. Unfortunately, often a significant fraction of the background is also released.

TABLE 6

IsoC*IsoG Stability as a Function of Salt Concentration

| Hybrid, Paired Oligonucleotide | Salt (M) | pH | AVG $T_m$ (° C.) | $\frac{dT_m}{d\log[Na+]}$ |
|---|---|---|---|---|
| isoC*isoG, 2*4 | 0.5 | 7.9 | 61 | |
| isoC*isoG, 2*4 | 0.17 | 7.9 | 56 | 10–11 |
| IsoC*isoG, 2*4 | 0.5 | 9.5 | 52 | |
| isoC*isoG, 2*4 | 0.17 | 9.5 | 50 | 3 |
| C*G, 1*3 | 0.5 | 9.5 | 52 | |
| C*G, 1*3 | 0.1 | 9.5 | 48.5 | 5 |

Because of the salt independence of the melt of the isoC*IsoG base pair at mildly alkaline pH, there is no additional advantage gained from lowering the salt as well as increasing the pH. Thus one can use high salt (which is also preferred for alkaline phosphatase) for the release and minimize the release of the background.

As explained in Example 3, the SELEX procedure could be used to find DNA or RNA sequences that show enhanced salt-independence in their melting at any selected pH.

Example 5

The Effect of Base Pair Mismatching on Hybridization

The previous examples showed that an oligomer with isoG base pairs specifically with its complement containing isoC. The isoG-containing oligomer is destabilized by about 7–8° C. when hybridized to another oligomer containing a single isoG*T or isoG*C mismatch. Typically, there is about a tenfold decrease in binding for each 10° C. degree change in $T_m$.

The effect of mismatching two bases on binding of a 13 mer hybrid was assessed using the probes shown in Table 7.

TABLE 7

| SEQ ID NO: | SEQUENCE[1] |
|---|---|
| 30 | 5'             GATGTGGTTGTCGTACTTTTTTTGACACTCCACCAT |
| 31 | 5'             GATGTGGTTGTCGTACTTTTTTTGACAFTCCJCCAT |
| 32 | ALK. PHOS.--   CTACACCAACAGCATGAA   5' |
| 33 | 3'             TCACTAAGTACCACCTCACAG |
| 34 | 5'             AGTGATTCATGGTGGAGTGTCTCTCTTGGAAAGAAAGTGAT |
| 35 | 3'             GAGAACCTTTCTTTCACTX |

[1]F = isoC, J = isoG, ALK. PHOS. = alkaline phosphatase, and X = a spacer sequence containing an amine for attachment to the solid support.

Labelled probe 32, the alkaline phosphatase oligonucleotide conjugate, was made as described (Urdea et al. (1988) *Nucl. Acids Res.* 16:4937–4955). Labelled probe 32 was hybridized with control probe 30 to create the alk. phos.-probe30*32. Labelled probe 32 was hybridized with modified probe 31 to create the isoC,isoG-alk. phos.-probe 31*32.

Probe 35, the capture probe, was bound to microtiter wells as described (PCT Publication No. WO91/813,338, the disclosure of which is incorporated by reference herein) to create a solid support for hybridization. Probe 34, a capture extender, was hybridized to probe 35. This capture extender is complementary to the alk. phos.-probe 30*32 and partially complementary to the alk. phos.-probe 31*32. Probe 33 is a "competimer" that can bind to the capture extender and block the binding of either alkaline phosphatase probe.

The following incubations were done for 30 min at 53° C. in approximately 1.0 M NaCl:

(1) 250 fmoles probe 34 in wells containing 1 pmole of immobilized probe 35;

(2) 250 fmoles probe 34+5 pmoles probe 33 in wells containing 1 pmole of immobilized probe 35;

(3) 5 pmoles probe 33 in wells containing 1 pmole of immobilized probe 35; and (4) buffer only.

After 2 washes with 0.1×SSC, 0.1% SDS, as defined in Example 1, each of the above first incubations was exposed to a second, 15 min. incubation under the same conditions with each of the following:

(1) 25 fmoles probe 30+500 attomoles probe 32;

(2) 25 fmoles probe 31+500 attomoles probe 32;

(3) 500 attomoles probe 32; and (4) buffer only.

The plates were washed twice as above and three times with the same buffer supplemented with 10 mM $MgCl_2$, 1 mM $ZnCl_2$, 0.1% Brij-35. After a 25 min. incubation with Lumiphos Plus (Lumigen) the plates were read on a Chiron luminometer.

Figure 3:
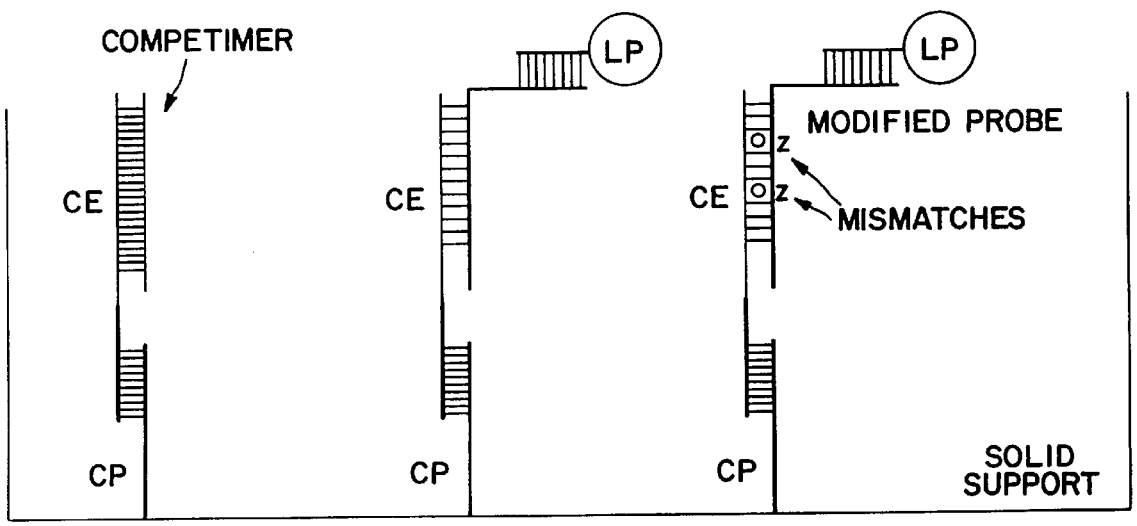
FIG. 3.

The hybrids that can form are depicted in FIG. 3, wherein Z, exemplified herein by isoC and isoG, represents a non-natural nucleotide. Probe 33, the competimer, can form 21 base pairs with the capture extender and in theory can block both alkaline phosphatase probes from binding. The modified probe*labelled probe (31*32) can hybridize to the capture extender, forming 11 base pairs and two mismatches (e.g., G*IsoC,isoG*T). The control probe*labelled probe (30*32) can form 13 base pairs with the capture extender.

As shown in Table 8, the capture extender (34) forms a strong hybrid with the control probe*labelled probe (30*32) (Sample 1=399 Relative Light Units (RLU)). Preincubation of the capture extender with a 20-fold molar excess of competimer, sample 2, reduced this background noise about tenfold (30 RLU). The modified probe*labelled probe (31*32) shows 40-fold less hybridization (sample 3=9 RLU) to the capture extender than control probe*labelled probe (30*32). The two mismatches accounted for a 40-fold change in hybridization. This is as expected for 2 mismatches, each of which destabilizes the $T_m$ by 7–8° C. (cf. 7×8=56-fold). The use of the competimer and the mismatched alk. phos. probe (sample 4=0.4 RLU), reduced the background noise about 1000-fold. Sample 5 is a control and has essentially no background noise (0.1 RLU). This is as expected since the labelled probe 32 has no detectable homology with the capture extender.

TABLE 8

The Effect of Base Pair Mismatching on Hybridization

| Sample No. | First Hybridization | Second Hybridization | AVG. RLU[1] (n = 6) | % CV[2] |
|---|---|---|---|---|
| 1 | 34 + 35 | 30 + 32 | 399 | 7 |
| 2 | 33 + 34 + 35 | 30 + 32 | 30 | 9 |
| 3 | 34 + 35 | 31 + 32 | 9 | 6 |
| 4 | 33 + 34 + 35 | 31 + 32 | 0.4 | 4 |
| 5 | 34 + 35 | 32 | 0.1 | 11 |

[1]RLU = Relative Light Units
[2]%CV = S.D./Avg. × 100

In hybridization assays, the use of competimers for all the capture extenders is impractical since there are typically 5–10 capture extenders per assay. In addition, this example shows that preincubation with the competimer was not as efficient as simply using 15% base substitution (with isoC, isoG), e.g., 2 bases out of 13, in the universal sequences. The use of 30% base substitution (3 out of 10) would be expected to reduce nonspecific hybridization of an otherwise perfectly basepaired complement by about 1000-fold (30% mismatch equals approximately 30° C. change in $T_m$; there is about a tenfold decrease in binding for each 10° C. change in $T_m$).

Example 6

Chemical Synthesis of 2'-deoxy-isoguanosine

The synthesis of 2'-deoxy-isoguanosine from 2'-deoxyguanosine was accomplished by the following procedure.

Step 1. 2'-Deoxyguanosine monohydrate (50 mmole) and imidazole (200 mmole) were dried by coevaporation with 500 mL dimethylformamide (DMF) and the residue dissolved in 500 mL DMF. To this solution was added t-butyldimethylsilyl chloride (150 mmole), and the reaction mixture was left stirring at room temperature for 18 hours. Methanol (30 mL) was added and after 25 minutes the solvents were removed in vacuo. The solvents were removed by evaporation, the residue dissolved in 1 L $CH_2Cl_2$, washed with 1 L 5% $NaHCO_3$ and 1 L 80% saturated NaCl, the organic phase dried over $Na_2SO_4$, filtered and evaporated to dryness yielded crude product (30 grams) which was directly dissolved in 2 L hot ethanol. Slow cooling to 20° C. followed by storage at 4° C. for 20 hours produced pure 3',5'-TBDMS$_2$-2'-deoxyguanosine (65% yield).

Step 2. 3',5'-TBDMS$_2$-2'-deoxyguanosine (12 mmole) was suspended in 125 mL $CH_2Cl_2$ containing triethylamine (150 mmole) and N,N-dimethylaminopyridine (100 mg). 4-Toluenesulfonyl chloride (40 mmole) was at 0° C., and the reaction mixture stirred at room temperature for 20 hours. At that time all solid material had dissolved resulting in a slightly yellow solution. The reaction was quenched with 50 mL 5% $NaHCO_3$ with stirring for 1 hour. The reaction mixture was diluted with 300 mL $CH_2Cl_2$, washed with 300 mL 5% $NaHCO_3$ and 300 mL 80% saturated NaCl, the organic phase dried over $Na_2SO_4$, filtered and evaporated to dryness yielded crude product (8.9 grams). Silica gel flash chromatography using a 1% to 4% methanol/$CH_2Cl_2$ gradient yielded 7.95 grams of pure $O^6$-(4-toluenesulfonyl)-3',5'-O-TBDMS$_2$-2,-deoxyguanosine (11 mmole).

Step 3. Twelve grams of $O^6$-(4-toluenesulfonyl)-3',5'-O-TBDMS$_2$-2'-deoxyguanosine (17 mmole) was suspended in 300 mL $CH_3CN$. Then methylpyrrolidine (17 mL) was added and the suspension stirred for one hour to produce a clear solution. TLC analysis showed that all starting material had been converted to base line material. Eleven grams of 4-(methylthio)phenol (85 mmole) was added and the solution stirred for 60 hours. After evaporation to a small volume 600 mL ethyl acetate was added. This solution was extracted with 3×400 mL of 0.3 M NaOH and 400 mL 80% saturated NaCl, the organic phase dried over $Na_2SO_4$, filtered and evaporated to dryness to yield 11.55 grams crude product. Silica gel flash chromatography using a 4% to 5% methanol/$CH_2Cl_2$ gradient yielded 8.16 grams of $O^6$-(4-(methylthio)phenyl)-3',5'-O-TBDMS$_2$-2'-deoxyguanosine (11 mmole).

Step 4. Four grams of $O^6$-(4-(methylthio)phenyl)-3',5'-O-TBDMS$_2$-2'-deoxyguanosine (6.5 mmole) was dissolved in 65 mL $CH_2Cl_2$ at 0° C. and 6.5 mL of tertbutyl nitrite was added dropwise. The solution was allowed to warm to room temperature and gas evolved from the mixture ($N_2$). After 40 minutes, when TLC analysis showed complete consumption of starting material and emergence of a new, slower migrating spot, excess t-butyl nitrite was removed by coevaporation with 2×100 mL toluene in vacuo. The residue of crude product was purified by silica gel flash chromatography using a 4% to 5% methanol/$CH_2Cl_2$ gradient to yield 2.75 grams of $O^6$-(4-(methylthio)phenyl)-3',5'-O-TBDMS$_2$-2'-deoxyxantosine (4.45 mmole).

Step 5. All of the purified 2.75 grams of $O^6$-(4-(methylthio)phenyl)-3',5'-O-TBDMS$_2$-2'-deoxyxantosine (4.45 mmole) was dissolved in 50 mL of methanol. Concentrated aqueous ammonium hydroxide (50 mL) was added and the mixture heated in a tightly sealed bomb at 100° C. for 4 hours. After cooling the solvents were removed by coevaporation with ethanol in vacuo to give 1.8 grams of crude product (3.6 mmole). Purification by recrystallization from hot ethanol yielded a sample of pure 3',5'-O-TBDMS$_2$-2'-deoxy-isoguanosine. This material was in every respect (UV, TLC, NMR and MS) identical to a sample prepared by the published, photolytic route (Switzer et al. (1993), supra).

Thus, novel methods for generating a more target-dependent signal in solution phase sandwich hybridization assays have been disclosed. In addition, a novel method for synthesizing 2'-deoxy-isoguanosine has been disclosed. Although preferred embodiments of the subject invention have been described in some detail, it is to be understood that obvious variations can be made without departing from the spirit and the scope of the invention as defined by the appended claims.

(1) GENERAL INFORMATION:

(iii) NUMBER OF SEQUENCES: 35

(2) INFORMATION FOR SEQ ID NO: 1:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

ATTGCGAATA ATAATTTTTT CACGTTGAAA ATCTTCTCTT GGAAAGAAAG TGAT         54

(2) INFORMATION FOR SEQ ID NO: 2:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

GAATTTCTTA AACAGCTTGA TACCGATAGT TGTTCTCTTG AAAGAAAGT GAT           53

(2) INFORMATION FOR SEQ ID NO: 3:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

ATTGTATCGG TTTATCAGCT TGCTTTCGAG GTTTCTCTTG AAAGAAAGT GAT           53

(2) INFORMATION FOR SEQ ID NO: 4:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CCGCTTTTGC GGGATCGTCA CCTTCTCTTG GAAAGAAAGT GAT                     43

(2) INFORMATION FOR SEQ ID NO: 5:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GCTGAGGCTT GCAGGGAGTT AAAGGTTCTC TTGGAAAGAA AGTGAT                  46

(2) INFORMATION FOR SEQ ID NO: 6:

(i) SEQUENCE CHARACTERISTICS:
        (A) LENGTH: 46 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO: 6:

ATGAGGAAGT TTCCATTAAA CGGGTTTCTC TTGGAAAGAA AGTGAT                46

(2) INFORMATION FOR SEQ ID NO: 7:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

TCGCCTGATA AATTGTGTCG AAATCCTTCT CTTGGAAAGA AAGTGAT               47

(2) INFORMATION FOR SEQ ID NO: 8:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

TCCAAAAAAA AAGGCTCCAA AAGGAGCCTT TATTCTCTTG GAAAGAAAGT GAT        53

(2) INFORMATION FOR SEQ ID NO: 9:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CGCCGACAAT GACAACAACC ATCGCTTCTC TTGGAAAGAA AGTGAT                46

(2) INFORMATION FOR SEQ ID NO: 10:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

ATGAGGAAGT TTCCATTAAA CGGGTTTAGG CATAGGACCC GTGTCT                46

(2) INFORMATION FOR SEQ ID NO: 11:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

GAGGCTTTGA GGACTAAAGA CTTTTTCTTA GGCATAGGAC CCGTGTCT                48

(2) INFORMATION FOR SEQ ID NO: 12:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 12:

CCCAGCGATT ATACCAAGCG CGTTAGGCAT AGGACCCGTG TCT                     43

(2) INFORMATION FOR SEQ ID NO: 13:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 13:

AAGAATACAC TAAAACACTC ATCTTTGACC TTAGGCATAG GACCCGTGTC T            51

(2) INFORMATION FOR SEQ ID NO: 14:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 14:

CTTTGAAAGA GGACAGATGA ACGGTGTTAG GCATAGGACC CGTGTCT                 47

(2) INFORMATION FOR SEQ ID NO: 15:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 15:

GGAACGAGGC GCAGACGGTC ATTAGGCATA GGACCCGTGT CT                      42

(2) INFORMATION FOR SEQ ID NO: 16:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 16:

ACGAGGGTAG CAACGGCTAC ATTAGGCATA GGACCCGTGT CT                      42

(2) INFORMATION FOR SEQ ID NO: 17:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GCGACCTGCT CCATGTTACT TAGCCTTAGG CATAGGACCC GTGTCT           46

(2) INFORMATION FOR SEQ ID NO: 18:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

CTCAGCAGCG AAAGACAGCA TCGGATTAGG CATAGGACCC GTGTCT           46

(2) INFORMATION FOR SEQ ID NO: 19:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

ATCATAAGGG AACCGAACTG ACCAATTAGG CATAGGACCC GTGTCT           46

(2) INFORMATION FOR SEQ ID NO: 20:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

CCACGCATAA CCGATATATT CGGTCTTAGG CATAGGACCC GTGTCT           46

(2) INFORMATION FOR SEQ ID NO: 21:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

TACAGACCAG GCGCATAGGC TGGCTTAGGC ATAGGACCCG TGTCT            45

(2) INFORMATION FOR SEQ ID NO: 22:

```
    (i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

AAACAAAGTA CAACGGAGAT TTGTATCATT AGGCATAGGA CCCGTGTCT            49

(2) INFORMATION FOR SEQ ID NO: 23:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

CACCAACCTA AAACGAAAGA GGCGATTAGG CATAGGACCC GTGTCT               46

(2) INFORMATION FOR SEQ ID NO: 24:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

AAAATACGTA ATGCCACTAC GAAGGTTAGG CATAGGACCC GTGTCT               46

(2) INFORMATION FOR SEQ ID NO: 25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_difference
        (B) LOCATION: replace(1, "")
        (D) OTHER INFORMATION: /note= "N = L = a primary amine.
            This nucleotide is not involved in the
            base-pairing."

(ix) FEATURE:
        (A) NAME/KEY: misc_difference
        (B) LOCATION: replace(15, "")
        (D) OTHER INFORMATION: /note= "This nucleotide is not
            involved in the base-pairing."

(xi) SEQUENCE DESCRIPTION: SEQ ID NO: 25:

NCACCACTTT CTCCT                                                 15

(2) INFORMATION FOR SEQ ID NO: 26:

(i) SEQUENCE CHARACTERISTICS:
        (A) LENGTH: 15 base pairs
        (B) TYPE: nucleic acid
        (C) STRANDEDNESS: single
        (D) TOPOLOGY: linear
```

(ii) MOLECULE TYPE: DNA (genomic)

(ix) FEATURE:
            (A) NAME/KEY: misc_difference
            (B) LOCATION: replace(1, "")
            (D) OTHER INFORMATION: /note= "N = L = a primary amine.
                This nucleotide is not involved in the
                base-pairing."

(ix) FEATURE:
            (A) NAME/KEY: misc_difference
            (B) LOCATION: replace(5, "")
            (D) OTHER INFORMATION: /note= "N = F = isoC."

(ix) FEATURE:
            (A) NAME/KEY: misc_difference
            (B) LOCATION: replace(15, "")
            (D) OTHER INFORMATION: /note= "This nucleotide is not
                involved in the base-pairing."

(xi) SEQUENCE DESCRIPTION: SEQ ID NO: 26:

NCACNACTTT CTCCT                                                    15

(2) INFORMATION FOR SEQ ID NO: 27:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_difference
            (B) LOCATION: replace(14, "")
            (D) OTHER INFORMATION: /note= "This nucleotide is not
                involved in the base-pairing."

(xi) SEQUENCE DESCRIPTION: SEQ ID NO: 27:

GGAGAAAGTG GTGT                                                     14

(2) INFORMATION FOR SEQ ID NO: 28:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_difference
            (B) LOCATION: replace(10, "")
            (D) OTHER INFORMATION: /note= "N = J = isoG."

(ix) FEATURE:
            (A) NAME/KEY: misc_difference
            (B) LOCATION: replace(14, "")
            (D) OTHER INFORMATION: /note= "This nucleotide is not
                invovled in the base-pairing."

(xi) SEQUENCE DESCRIPTION: SEQ ID NO: 28:

GGAGAAAGTN GTGT                                                     14

(2) INFORMATION FOR SEQ ID NO: 29:

(i) SEQUENCE CHARACTERISTICS:
            (A) LENGTH: 14 base pairs
            (B) TYPE: nucleic acid
            (C) STRANDEDNESS: single
            (D) TOPOLOGY: linear

```
        (ii) MOLECULE TYPE: DNA (genomic)

(ix) FEATURE:
              (A) NAME/KEY: misc_difference
              (B) LOCATION: replace(14, "")
              (D) OTHER INFORMATION: /note= "This nucleotide is not
                  involved in the base-pairing."

(xi) SEQUENCE DESCRIPTION: SEQ ID NO: 29:

CACTACTTTC TCCT                                                            14

(2) INFORMATION FOR SEQ ID NO: 30:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 30:

GATGTGGTTG TCGTACTTTT TTTGACACTC CACCAT                                    36

(2) INFORMATION FOR SEQ ID NO: 31:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: misc_difference
              (B) LOCATION: replace(28, "")
              (D) OTHER INFORMATION: /note= "N = F = isoC."

(ix) FEATURE:
              (A) NAME/KEY: misc_difference
              (B) LOCATION: replace(32, "")
              (D) OTHER INFORMATION: /note= "N = J = isoG."

(xi) SEQUENCE DESCRIPTION: SEQ ID NO: 31:

GATGTGGTTG TCGTACTTTT TTTGACANTC CNCCAT                                    36

(2) INFORMATION FOR SEQ ID NO: 32:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 32:

AAGTACGACA ACCACATC                                                        18

(2) INFORMATION FOR SEQ ID NO: 33:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: DNA (genomic)
```

(xi) SEQUENCE DESCRIPTION: SEQ ID NO: 33:

GACACTCCAC CATGAATCAC T                                                  21

(2) INFORMATION FOR SEQ ID NO: 34:

(i) SEQUENCE CHARACTERISTICS:
                (A) LENGTH: 41 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO: 34:

AGTGATTCAT GGTGGAGTGT CTCTCTTGGA AAGAAAGTGA T                              41

(2) INFORMATION FOR SEQ ID NO: 35:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: misc_difference
                (B) LOCATION: replace(1, "")
                (D) OTHER INFORMATION: /note= "N = X = a spacer sequence
                     contaning an amine for attachment to the solid
                     support."

(xi) SEQUENCE DESCRIPTION: SEQ ID NO: 35:

NTCACTTTCT TTCCAAGAG                                                      19

We claim:

1. A method for synthesizing a compound having the structural formula

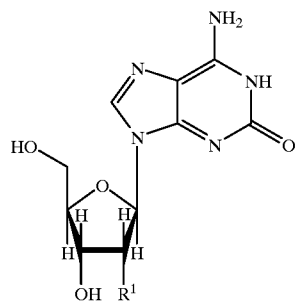

wherein $R^1$ is selected from the group consisting of hydrogen, hydroxyl, sulfhydryl, halogeno, amino, alkyl, allyl and $-OR^2$, wherein $R^2$ is selected from the group consisting of alkyl, allyl, silyl and phosphate, comprising:

a) reacting a compound having the structural formula

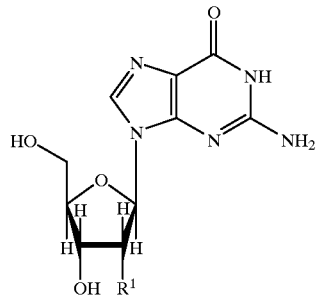

with a protecting reagent suitable to protect both the 3' and 5' hydroxyl groups, thus providing an intermediate having the structural formula

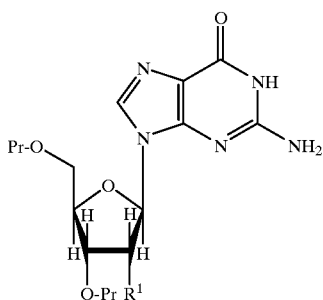

in which Pr represents a hydroxyl-protecting group;

b) reacting the product of step (a) with a reagent suitable to convert the $O^6$-oxy moiety into a functional group that is susceptible to nucleophilic displacement, thereby producing a functionalized $O^6$ moiety;

c) oxidizing the 2-amino group of the product of step (b) with an oxidizing agent;

d) reacting the product of step (c) with $NH_4OH$ to displace the functionalized $O^6$ moiety; and e) reacting the product of step (d) with a reagent suitable to deprotect the protected 3' and 5' hydroxyl groups.

2. A method for synthesizing 2'-deoxy-isoguanosine comprising:

a) converting 2'-deoxyguanosine to 3',5'-O-(t-butyldimethylsilyl)2-2'-deoxyguanosine by reacting 2'-deoxyguanosine with t-butyldimethylsilyl (TBDMS) chloride;

b) converting 3',5'-O-$TBDMS_2$-2'-deoxyguanosine to $O^6$-(4-toluenesulfonyl)-3',5'-O-$TBDMS_2$-2'-deoxyguanosine by reacting 3',5'-O-$TBDMS_2$-2'-deoxyguanosine with 4-toluenesulfonyl chloride;

c) displacing the $O^6$-(4-toluenesulfonyl) group by treating $O^6$-(4-toluenesulfonyl)-3',5'-O-$TBDMS_2$-2'-deoxyguanosine with a phenol to give $O^6$-(4-(methylthio)phenyl)-3',5'-O-$TBDMS_2$-2'-deoxyguanosine;

d) oxidizing the 2-amino group of $O^6$-(4-(methylthio)phenyl)-3',5'-O-$TBDMS_2$-2'-deoxyguanosine to the oxy function by treating $O^6$-(4-(methylthio)phenyl)-3',5'-O-$TBDMS_2$-2'-deoxyguanosine with t-butyl nitrite under neutral conditions to give $O^6$-(4-(methylthio)phenyl)-3',5'-O-$TBDMS_2$-2'-deoxyxantosine; and e) displacing the $O^2$-(4-(methylthio)phenyl) group of $O^6$-(4-(methylthio)phenyl)-3',5'-O-$TBDMS_2$-2'-deoxyxantosine with ammonium hydroxide at elevated temperature to give 3',5'-O-$TBDMS_2$-2'-deoxy-isoguanosine.

3. The method of claim 1, wherein the protecting reagent is selected from the group consisting of tert-butyldimethylsilyl chloride, benzoyl chloride, and acetic anhydride.

4. The method of claim 1, wherein the functionalized $O^6$ moiety is selected from the group consisting of $CH_3$—S—$C_6H_4$—$O^6$—, $C_6H_5$—$SO_2$—$O^6$—, $C_6H_5$—$O^6$—, 4-nitro-$C_6H_4$—$O^6$—, and 2,4,6-trinitro-$C_6H_2$—$O^6$—.

5. The method of claim 1, wherein the oxidizing agent is an alkyl nitrite.

6. The method of claim 1, wherein the reagent suitable to deprotect the protected 3' and 5' hydroxyl groups is selected from the group consisting of basic reagents and fluoride-containing reagents.

* * * * *